United States Patent
Koizumi et al.

(10) Patent No.: US 11,857,544 B2
(45) Date of Patent: Jan. 2, 2024

(54) COMPOSITION OR METHOD INCLUDING (T)EW-7197 FOR TREATING OR PREVENTING CORNEAL ENDOTHELIAL DISEASES

(71) Applicants: THE DOSHISHA, Kyoto (JP); SENJU PHARMACEUTICAL CO., LTD., Osaka (JP)

(72) Inventors: Noriko Koizumi, Kyotanabe (JP); Naoki Okumura, Kyotanabe (JP); Mayumi Yamamoto, Osaka (JP)

(73) Assignees: THE DOSHISHA, Kyoto (JP); SENJU PHARMACEUTICAL CO., LTD., Osaka (JP)

( * ) Notice: Subject to any disclaimer, the term of this patent is extended or adjusted under 35 U.S.C. 154(b) by 90 days.

(21) Appl. No.: 16/772,384

(22) PCT Filed: Dec. 13, 2018

(86) PCT No.: PCT/JP2018/045919
§ 371 (c)(1),
(2) Date: Jun. 12, 2020

(87) PCT Pub. No.: WO2019/117254
PCT Pub. Date: Jun. 20, 2019

(65) Prior Publication Data
US 2021/0077476 A1 Mar. 18, 2021

(30) Foreign Application Priority Data

Dec. 13, 2017 (JP) ................. 2017-239049
Sep. 28, 2018 (JP) ................. 2018-184783

(51) Int. Cl.
*A61K 31/444* (2006.01)
*A61P 27/02* (2006.01)
*A61K 9/00* (2006.01)
*A61K 9/08* (2006.01)
*A61K 47/02* (2006.01)

(52) U.S. Cl.
CPC .......... *A61K 31/444* (2013.01); *A61K 9/0048* (2013.01); *A61K 9/08* (2013.01); *A61K 47/02* (2013.01); *A61P 27/02* (2018.01)

(58) Field of Classification Search
CPC .................................................. A61K 31/444
See application file for complete search history.

(56) References Cited

U.S. PATENT DOCUMENTS

| 2011/0319406 A1* | 12/2011 | Kim .................. A61P 31/18 514/233.2 |
| 2016/0158210 A1 | 6/2016 | Koizumi et al. |
| 2016/0296505 A1 | 10/2016 | Koizumi et al. |

FOREIGN PATENT DOCUMENTS

| JP | 2013-533252 A | 8/2013 | |
| WO | WO 2012/002680 A2 | 1/2012 | |
| WO | WO 2015/064768 A1 | 5/2015 | |
| WO | WO2015/064798 * | 5/2015 | ........... A61K 31/519 |

OTHER PUBLICATIONS

Jin et al., "Discovery of N-((4-([1,2,4]Triazolo[1,5-α]pyridin-6-yl)-5-(6-methylpyridin-2-yl)-1H-imidazol-2-yl)methyl)-2-fluoroaniline (EW-7197): A Highly Potent, Selective, and Orally Bioavalable Inhibitor of TFF-β Type I Receptor Kinase as Cancer Immunotherapeutic/Antifibrotic Agent," *J. Med. Chem.*, 57: 4213-4238 (2014).

Naka et al., "Novel oral transforming growth factor-β signaling inhibitor EW-7197 eradicates CML-initiating cells," *Cancer Sci.*, 107(2): 140-148 (2016).

European Patent Office, Extended European Search Report in European Patent Application No. 18888179.1 (dated Oct. 20, 2021).

Callahan et al., "Identification of Novel Inhibitors of the Transforming Growth Factor β1 (TGF-β1) Type 1 Receptor (ALK5)," *J. Med. Chem.*, 45(5): 999-1001 (2002).

Japanese Patent Office, International Search Report in International Patent Application No. PCT/JP2018/045919 (dated Mar. 19, 2019).

Japan Patent Office, Notice of Reasons for Refusal in Japanese Application No. 2019-559203 (dated Feb. 2, 2023) machine English translation.

Russian Federal Service for Intellectual Property, Official Action in Russian Patent Application No. 2020122861/04 (dated Dec. 23, 2022) English translation.

Federal Service for Intellectual Property, Official Action in Russian Patent Application No. 2020122861/04(039341) (dated May 23, 2022).

China National Intellectual Property Administration, Search Report in Chinese Patent Application No. 201880088873.9 (dated Oct. 19, 2022).

China National Intellectual Property Administration, Office Action in Chinese Patent Application No. 201880088873.9 (dated Oct. 26, 2022).

Callahan et al., "Identification of Novel Inhibitors of the Transforming Growth Factor β1 (TGF- β1) Type 1 Receptor," *J. Med. Chem.*, 45(5): 999-1001 (2002).

* cited by examiner

*Primary Examiner* — Paul V Ward
(74) *Attorney, Agent, or Firm* — Leydig, Voit & Mayer, Ltd.

(57) ABSTRACT

The present disclosure provides a composition for treating or preventing symptoms, disorders, or diseases of the corneal endothelium. The present invention specifically provides a composition which is for treating or preventing symptoms, disorders, or diseases of the corneal endothelium, and includes (T)EW-7197 (N-((4-([1,2,4]triazolo[1,5-a]pyridin-6-yl)-5-(6-methylpyridin-2-yl)-1H-imidazol-2-yl)methyl)-2-fluoroaniline), a derivative thereof, a pharmaceutically acceptable salt thereof, or a solvate of any of the foregoing.

10 Claims, 9 Drawing Sheets

Fig.1
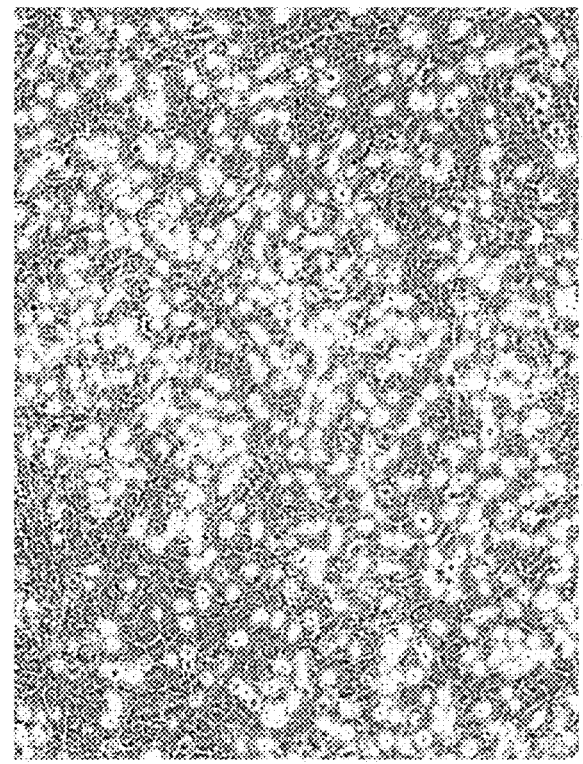
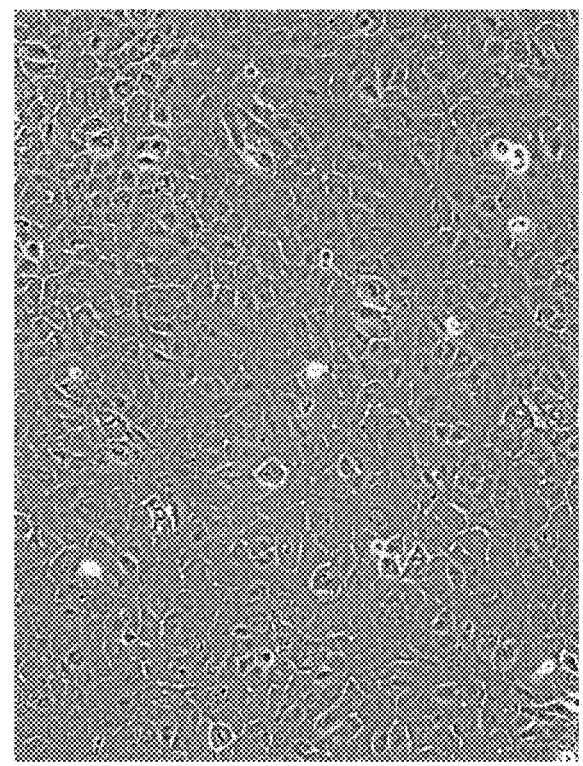

Fig.3

| (μM) | SB431542 | EW-7197 |
|---|---|---|
| 0.1 | × | ◎ |
| 0.3 | × | ◎ |
| 1 | × | ◎ |
| 3 | ○ | △ |
| 10 | ◎ | △ |

◎ : Near complete suppression of TGF-$\beta$ action
○ : Strong suppression of TGF-$\beta$ action
△ : Has effect of suppressing TGF-$\beta$ action
× : No effect of suppressing TGF-$\beta$ action is found

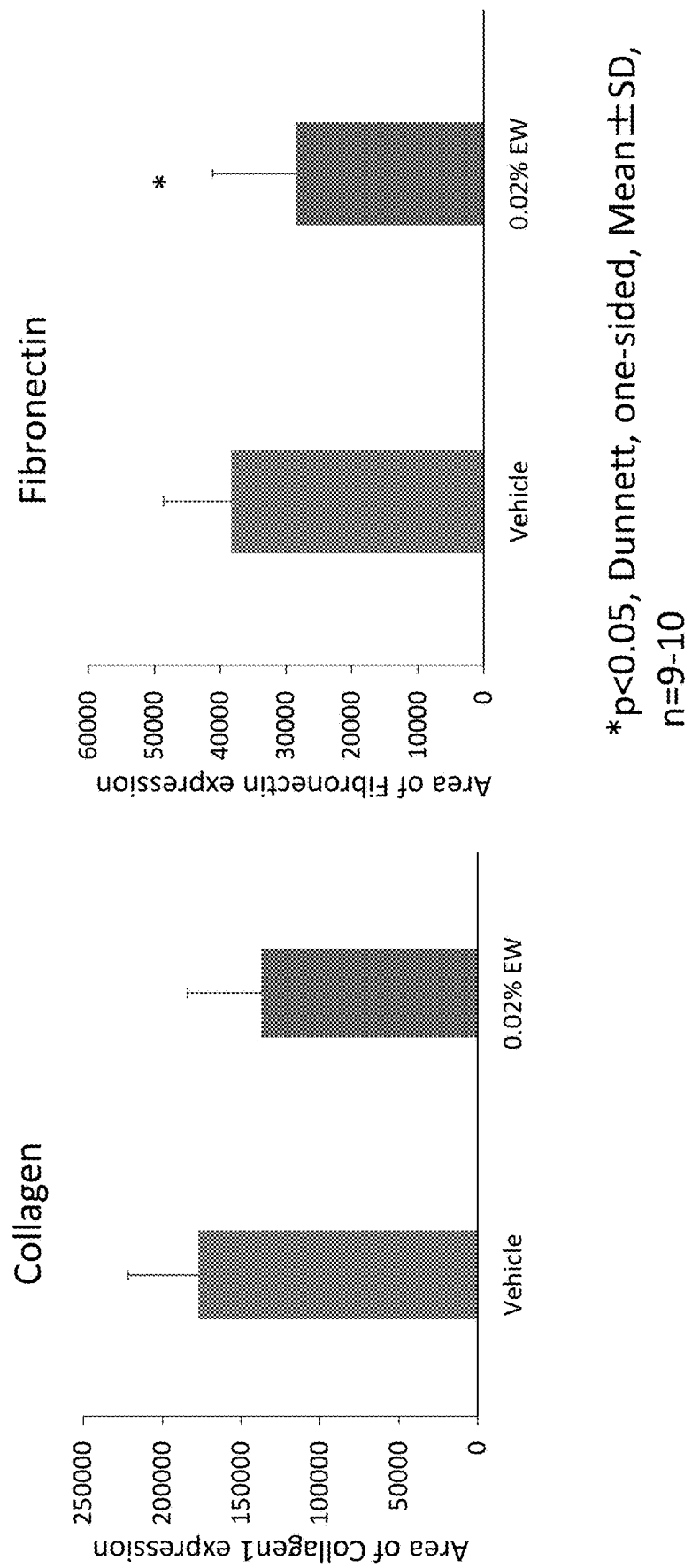

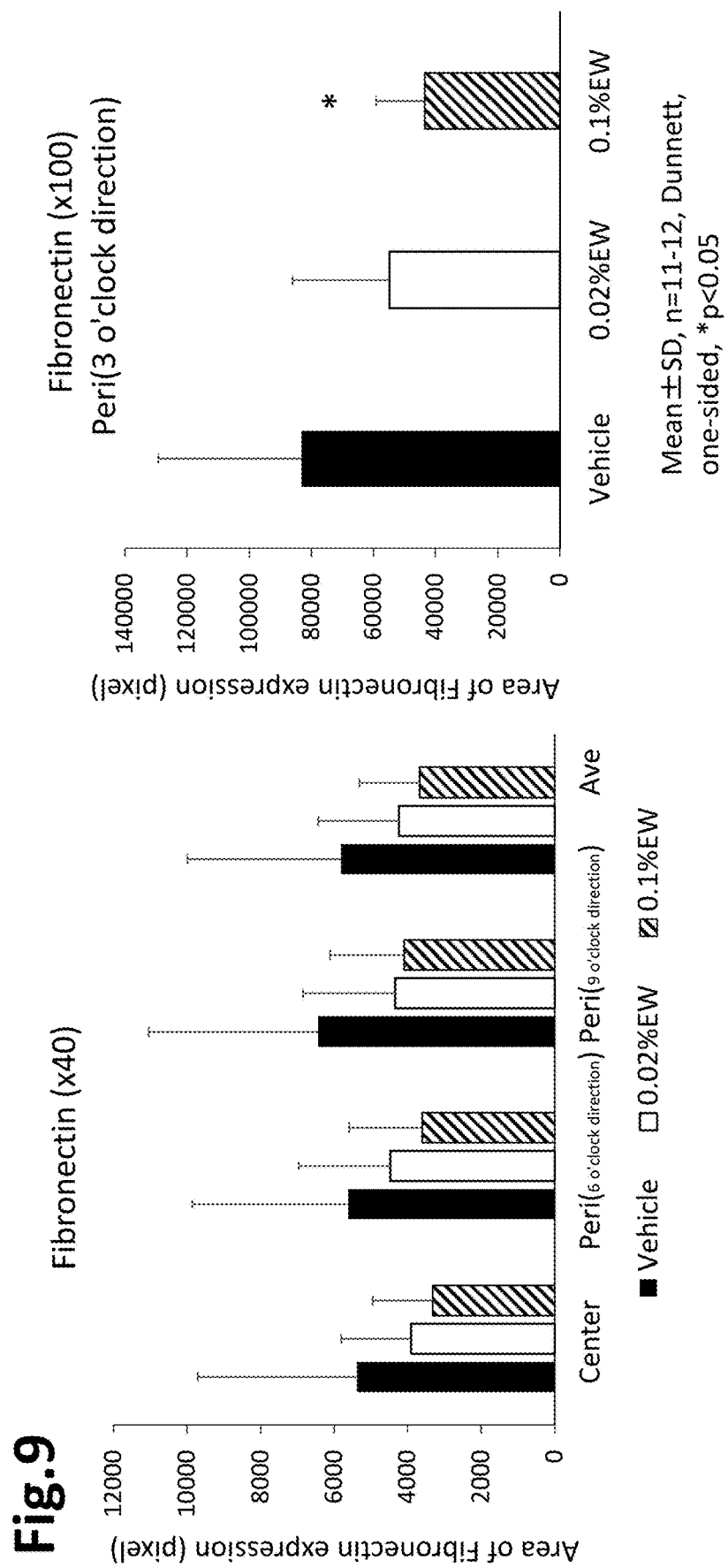

COMPOSITION OR METHOD INCLUDING (T)EW-7197 FOR TREATING OR PREVENTING CORNEAL ENDOTHELIAL DISEASES

CROSS-REFERENCE TO RELATED APPLICATIONS

This patent application is the U.S. national phase of International Patent Application No. PCT/JP2018/045919, filed on Dec. 13, 2018, which claims the benefit of Japanese Patent Application No. 2017-239049 filed on Dec. 13, 2017 and Japanese Patent Application No. 2018-184783 filed on Sep. 28, 2018, which are incorporated by reference in their entireties herein.

TECHNICAL FIELD

The present invention relates to a novel use of (T)EW-7197. More specifically, the present invention relates to a technology, method, or agent for treating or preventing a corneal endothelial condition, disorder, or disease, comprising (T)EW-7197 (N-((4-([1,2,4]triazolo[1,5-a]pyridin-6-yl)-5-(6-methylpyridin-2-yl)-1H-imidazol-2-yl)methyl)-2-fluoroaniline) or a derivative thereof, or a pharmaceutically acceptable salt thereof, or a solvate thereof, and a technology for preserving corneal endothelial cells applying such a technology.

BACKGROUND ART

Visual information is recognized when light transmitted into the cornea, which is a transparent tissue at the frontmost part of an eye ball, reaches the retina and excites nerve cells of the retina, and a generated electric signal is transmitted through the optic nerve to the visual cortex of the cerebrum. To attain good vision, it is necessary that the cornea is transparent. The transparency of the cornea is maintained by maintaining constant water content by the pump and barrier functions of corneal endothelial cells.

While human corneal endothelial cells are present at a density of about 3000 cells per 1 mm$^2$ at birth, once damaged, the ability to regeneration is very limited. One of the corneal endothelial disorders, Fuchs' endothelial corneal dystrophy, is a disease causing an abnormality in endothelial cells inside the cornea, resulting in corneal edema. The cause thereof is unknown. In Fuchs' endothelial corneal dystrophy, extracellular matrix such as collagen is deposited on a part of the back surface of a Descemet's membrane at the back of the cornea, resulting in corneal guttae and thickening of the Descemet's membrane. Corneal guttae and thickening of the Descemet's membrane are causes of glare or blurred vision in Fuchs' endothelial corneal dystrophy patients, which compromises the QOL of the patients. It is understood that there is no effective therapeutic method other than corneal transplantation for Fuchs' endothelial corneal dystrophy. However, there is a shortage in cornea donation in Japan, where patients waiting for corneal transplantation is about 2600, whereas the number of corneal transplantation performed in Japan is about 1700 annually.

SUMMARY OF INVENTION

Solution to Problem

The inventors found that (T)EW-7197 (N-((4-([1,2,4]triazolo[1,5-a]pyridin-6-yl)-5-(6-methylpyridin-2-yl)-1H-imidazol-2-yl)methyl)-2-fluoroaniline) with the following structure:

[Chemical Formula 1]

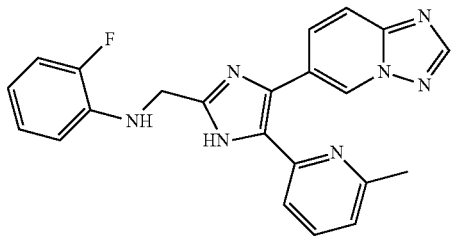

exhibits very good effect of suppressing cellular disorders in cells of a corneal endothelial disorder model. The effect of suppressing cellular disorders of (T)EW-7197 was confirmed even at a very low concentration. In addition, the inventors also found that (T)EW-7197 can suppress the expression of extracellular matrix (ECM) such as fibronectin, to treat ECM abnormalities in corneal endothelial disorders in cells of a corneal endothelial disorder model.

Therefore, the present invention provides, for example, the following items.

(Item 1)
A composition for treating or preventing a corneal endothelial condition, disorder, or disease, comprising (T)EW-7197 (N-((4-([1,2,4]triazolo[1,5-a]pyridin-6-yl)-5-(6-methylpyridin-2-yl)-1H-imidazol-2-yl)methyl)-2-fluoroaniline) or a derivative thereof, or a pharmaceutically acceptable salt thereof, or a solvate thereof.

(Item 2)
The composition of item 1, wherein the composition is for suppressing a reduction in a corneal endothelial cell density.

(Item 3)
The composition of item 1 or 2, wherein the corneal endothelial condition, disorder, or disease is Fuchs' endothelial corneal dystrophy or corneal guttata.

(Item 4) The composition of item 1, wherein the corneal endothelial condition, disorder, or disease is due to overexpression of extracellular matrix (ECM).

(Item 5)
The composition of item 4, wherein the extracellular matrix (ECM) is selected from the group consisting of type I collagen, type IV collage, type V collage, and fibronectin.

(Item 6)
The composition of item 4 or 5, wherein the corneal endothelial condition, disorder, or disease is selected from the group consisting of Fuchs' endothelial corneal dystrophy, guttae formation, thickening of a Descemet's membrane, thickening of a cornea, corneal opacity, scar, corneal nebula, corneal macula, leukoma, glare, and blurred vision.

(Item 7)
The pharmaceutical composition of any one of items 1 to 6, wherein the corneal endothelial condition, disorder, or disease is in Fuchs' endothelial corneal dystrophy.

(Item 8)
The composition of any one of items 1 to 7, wherein the (T)EW-7197 or a derivative thereof, or a pharmaceutically acceptable salt thereof, or a solvate thereof is in the composition at a concentration of about 0.001 mM to about 10 mM.

(Item 9)
The composition of any one of items 1 to 8, wherein the (T)EW-7197 or a derivative thereof, or a pharmaceutically acceptable salt thereof, or a solvate thereof is in the composition at a concentration of about 0.01 mM to about 5 mM.

(Item 10)

The composition of any one of items 1 to 9, which is an eye drop.

(Item A1)

A method of treating or preventing a corneal endothelial condition, disorder, or disease in a subject, comprising administering to the subject an effective amount of (T)EW-7197 (N-((4-([1,2,4]triazolo[1,5-a]pyridin-6-yl)-5-(6-methylpyridin-2-yl)-1H-imidazol-2-yl)methyl)-2-fluoroaniline) or a derivative thereof, or a pharmaceutically acceptable salt thereof, or a solvate thereof.

(Item A2)

The method of item A1, wherein the method suppresses a reduction in a corneal endothelial cell density.

(Item A3)

The method of item A1 or A2, wherein the corneal endothelial condition, disorder, or disease is Fuchs' endothelial corneal dystrophy or corneal guttata.

(Item A4)

The method of item A1, wherein the corneal endothelial condition, disorder, or disease is due to overexpression of extracellular matrix (ECM).

(Item A5)

The method of item A4, wherein the extracellular matrix (ECM) is selected from the group consisting of type I collagen, type IV collage, type V collage, and fibronectin.

(Item A6)

The method of item A4 or A5, wherein the corneal endothelial condition, disorder, or disease is selected from the group consisting of Fuchs' endothelial corneal dystrophy, guttae formation, Thickening of a Descemet's membrane, Thickening of a cornea, corneal opacity, scar, corneal nebula, corneal macula, leukoma, glare, and blurred vision.

(Item A7)

The method of any one of items A1 to A6, wherein the corneal endothelial condition, disorder, or disease is in Fuchs' endothelial corneal dystrophy.

(Item A8)

The method of any one of items A1 to A7, wherein the (T)EW-7197 or a derivative thereof, or a pharmaceutically acceptable salt thereof, or a solvate thereof is administered at a concentration of about 0.001 mM to about 10 mM.

(Item A9)

The method of any one of items A1 to A8, wherein the (T)EW-7197 or a derivative thereof, or a pharmaceutically acceptable salt thereof, or a solvate thereof is administered at a concentration of about 0.01 mM to about 5 mM.

(Item A10)

The method of any one of items A1 to A9, wherein the (T)EW-7197 or a derivative thereof, or a pharmaceutically acceptable salt thereof, or a solvate thereof is administered as an eye drop.

(Item B1)

Use of (T)EW-7197 (N-((4-([1,2,4]triazolo[1,5-a]pyridin-6-yl)-5-(6-methylpyridin-2-yl)-1H-imidazol-2-yl)methyl)-2-fluoroaniline) or a derivative thereof, or a pharmaceutically acceptable salt thereof, or a solvate thereof in the manufacture of a medicament for treating or preventing a corneal endothelial condition, disorder, or disease.

(Item B2)

The use of item B1, wherein the medicament is for suppressing a reduction in a corneal endothelial cell density.

(Item B3)

The use of item B1 or B2, wherein the corneal endothelial condition, disorder, or disease is Fuchs' endothelial corneal dystrophy or corneal guttata.

(Item B4) The use of item B1, wherein the corneal endothelial condition, disorder, or disease is due to overexpression of extracellular matrix (ECM).

(Item B5)

The use of item B4, wherein the extracellular matrix (ECM) is selected from the group consisting of type I collagen, type IV collage, type V collage, and fibronectin.

(Item B6)

The use of item B4 or B5, wherein the corneal endothelial condition, disorder, or disease is selected from the group consisting of Fuchs' endothelial corneal dystrophy, guttae formation, thickening of a Descemet's membrane, thickening of a cornea, corneal opacity, scar, corneal nebula, corneal macula, leukoma, glare, and blurred vision.

(Item B7)

The use of any one of items B1 to B6, wherein the corneal endothelial condition, disorder, or disease is in Fuchs' endothelial corneal dystrophy.

(Item B8) The use of any one of items B1 to B7, wherein the (T)EW-7197 or a derivative thereof, or a pharmaceutically acceptable salt thereof, or a solvate thereof is in the composition at a concentration of about 0.001 mM to about 10 mM.

(Item B9)

The use of any one of items B1 to B8, wherein the (T)EW-7197 or a derivative thereof, or a pharmaceutically acceptable salt thereof, or a solvate thereof is in the medicament at a concentration of about 0.01 mM to about 5 mM.

(Item B10)

The use of any one of items B1 to B9, wherein the medicament is an eye drop.

(Item C1) A compound for use in treating or preventing a corneal endothelial condition, disorder, or disease, wherein the compound is (T)EW-7197 (N-((4-([1,2,4]triazolo[1,5-a]pyridin-6-yl)-5-(6-methylpyridin-2-yl)-1H-imidazol-2-yl)methyl)-2-fluoroaniline) or a derivative thereof, or a pharmaceutically acceptable salt thereof, or a solvate thereof.

(Item C2)

The compound of item C1, wherein the compound is for use in suppressing a reduction in a corneal endothelial cell density.

(Item C3)

The compound of item C1 or C2, wherein the corneal endothelial condition, disorder, or disease is Fuchs' endothelial corneal dystrophy or corneal guttata.

(Item C4)

The compound of item C1, wherein the corneal endothelial condition, disorder, or disease is due to overexpression of extracellular matrix (ECM).

(Item C5) The compound of item C4, wherein the extracellular matrix (ECM) is selected from the group consisting of type I collagen, type IV collage, type V collage, and fibronectin.

(Item C6) The compound of item C4 or C5, wherein the corneal endothelial condition, disorder, or disease is selected from the group consisting of Fuchs' endothelial corneal dystrophy, guttae formation, thickening of a Descemet's membrane, thickening of a cornea, corneal opacity, scar, corneal nebula, corneal macula, leukoma, glare, and blurred vision.

(Item C7)

The compound of any one of items C1 to C6, wherein the corneal endothelial condition, disorder, or disease is in Fuchs' endothelial corneal dystrophy.

(Item C8)

The compound of any one of items C1 to C7, wherein the compound is administered at a concentration of about 0.001 mM to about 10 mM.

(Item C9)

The compound of any one of items C1 to C8, wherein the compound is administered at a concentration of about 0.01 mM to about 5 mM.

(Item C10)

The compound of any one of items C1 to C9, wherein the compound is administered as an eye drop.

The present invention is intended to be able to provide one or more of the aforementioned features in further combinations in addition to the combinations expressly shown. Further embodiments and advantages of the invention are recognized by those skilled in the art by reading and understanding the following Detailed Description as needed.

Advantageous Effects of Invention

The present invention provides a medicament that can treat or prevent a corneal endothelial condition, disorder, or disease, comprising (T)EW-7197 (N-((4-([1,2,4]triazolo[1,5-a]pyridin-6-yl)-5-(6-methylpyridin-2-yl)-1H-imidazol-2-yl)methyl)-2-fluoroaniline) or a derivative thereof, or a pharmaceutically acceptable salt thereof, or a solvate thereof. Furthermore, the present invention provides a composition for preserving a corneal endothelial cell or a composition for promoting the growth of a corneal endothelial cell, comprising (T)EW-7197 or a derivative thereof, or a pharmaceutically acceptable salt thereof, or a solvate thereof.

BRIEF DESCRIPTION OF DRAWINGS

FIG. 1 shows phase contrast microscope pictures of immortalized corneal endothelial cells derived from a Fuchs' endothelial corneal dystrophy patient (iFECD), which is a corneal endothelial disorder model (left: without TGF-β addition, right: with TGF-β addition).

FIG. 3 shows a table summarizing the evaluation of the effect of suppressing cellular disorders in iFECD observed in FIG. 2.

FIG. 8 shows the results of analyzing the area of type I collagen and fibronectin expression in a 0.02% EW-7197 eye drop group and base agent ("vehicle") eye drop group. The vertical axis indicates the area of expression (pixel).

FIG. 9 shows the results of analyzing area of fibronectin expression in 0.02% and 0.1% EW-7197 eye drop groups and base agent ("vehicle") eye drop group. The vertical axis indicates the area of expression (pixel). The left graph shows results of analysis after cutting out luminescence of 30000 or less in the field of vision at 40 times magnification (center, 6 o'clock direction and 9 o'clock direction (ear side)). The right graph shows results of analysis in the field of vision at 100 times magnification (3 o'clock direction (nose side)).

DESCRIPTION OF EMBODIMENTS

Figure 2:
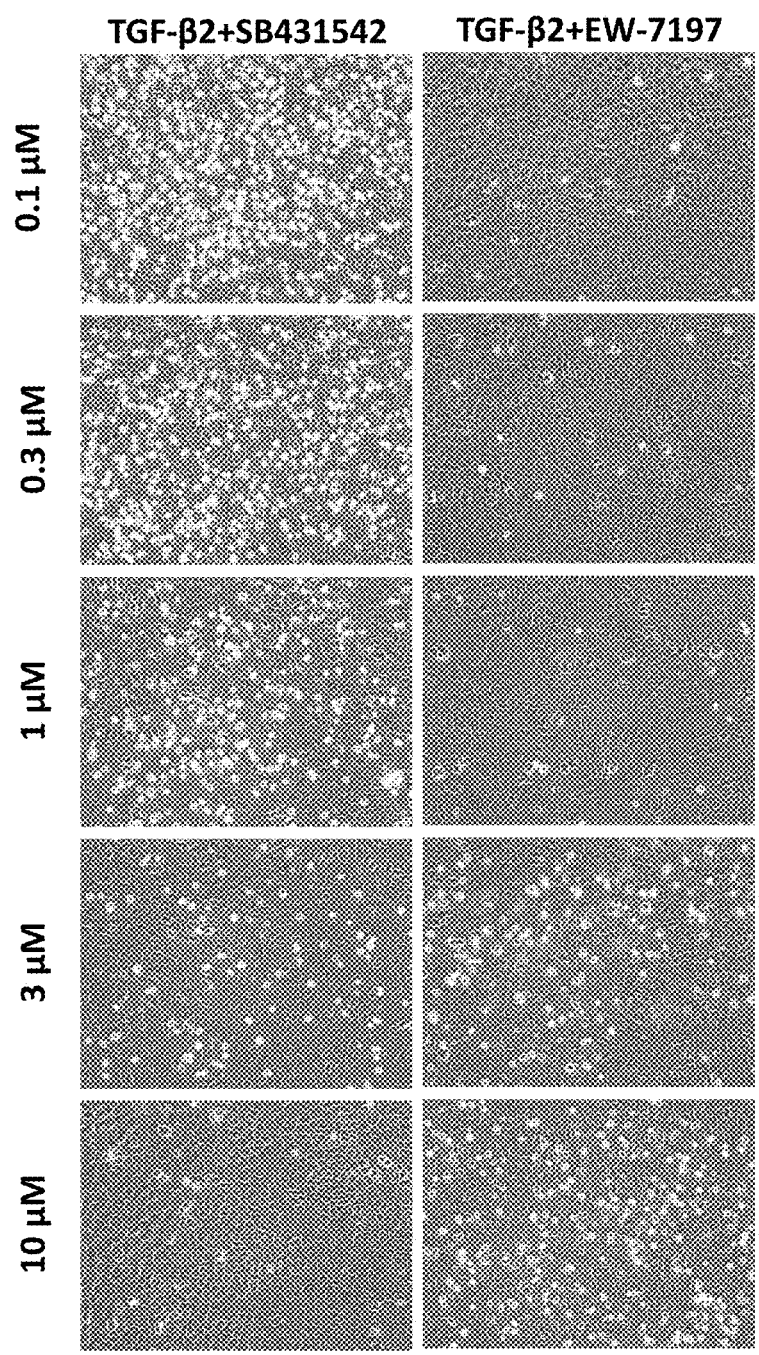
FIG. 2 shows phase contrast microscope pictures of immortalized corneal endothelial cells derived from a Fuchs' endothelial corneal dystrophy patient (iFECD) treated with EW-7197 and SB431542.

The present invention is described hereinafter. Throughout the entire specification, a singular expression should be understood as encompassing the concept thereof in the plural form, unless specifically noted otherwise. Thus, singular articles (e.g., "a", "an", "the", and the like in the case of English) should also be understood as encompassing the concept thereof in the plural form, unless specifically noted otherwise. Further, the terms used herein should be understood as being used in the meaning that is commonly used in the art, unless specifically noted otherwise. Therefore, unless defined otherwise, all terminologies and scientific technical terms that are used herein have the same meaning as the general understanding of those skilled in the art to which the present invention pertains. In case of a contradiction, the present specification (including the definitions) takes precedence.

Definitions

As used herein, "about" refers to a range of ±10% of the subsequent numerical value, unless specifically noted otherwise.

As used herein, a "subject" refers to a target of administration (transplant) of a therapeutic or preventive medicament or method of the invention. Examples of subjects include mammals (e.g., human, mouse, rat, hamster, rabbit, cat, dog, cow, horse, sheep, monkey, and the like), but primates are preferable and humans are particularly preferable.

As used herein, "EW-7197" and "TEW-7197" are used interchangeably, referring to N-((4-([1,2,4]triazolo[1,5-a]pyridin-6-yl)-5-(6-methylpyridin-2-yl)-1H-imidazol-2-yl)methyl)-2-fluoroaniline. "EW-7197" and "TEW-7197" are also collectively denoted herein as "(T)EW-7197".

As used herein, a corneal endothelial condition, disorder, or disease "due to overexpression of extracellular matrix (ECM)" is mainly a corneal endothelial condition, disorder, or disease associated with clouding, deposition, hypertrophy, or the like due to extracellular matrix, or a condition that causes reduced vision from guttata on the corneal endothelium surface, thickening of the Descemet's membrane such as turbid guttae of the Descemet's membrane, or the like. In corneal endothelial disorders such as Fuchs' corneal dystrophy, overproduction of extracellular matrix worsens the vision or visual sense even without a reduction in cell count, unlike exacerbation in a condition due to death (particularly apoptosis) of corneal endothelial cells. Thus, even if cell death can be suppressed, this needs to be addressed.

As used herein, "derivative" refers to a compound with a chemical or physical modification such as a functional group that has the same or similar core structure as that of the parent compound but is different, or an additional functional group. A derivative has the same or similar biological activity as the parent compound.

As used herein, "pharmaceutically acceptable salt" refers to an inorganic or organic acid addition salt of the compound of the invention that is relatively non-toxic. These salts can be prepared by reacting a compound purified temporarily between the final isolation and purification of a compound or by a free base form separately with a suitable organic or inorganic salt, and isolating a salt formed in this manner.

Examples of pharmaceutically acceptable basic salts of the compound of the invention include alkali metal salts such as sodium salts and potassium salts; alkaline earth metal salts such as calcium salts and magnesium salts; ammonium salts; aliphatic amine salts such as trimethylamine salts, triethylamine salts, dicyclohexylamine salts, ethanolamine salts, diethanolamine salts, triethanolamine salts, procaine salts, meglumine salts, diethanolamine salts, and ethylenediamine salts; aralkylamine salts such as N,N-dibenzylethylenediamine and benetamine salts; heterocyclic aromatic amine salts such as pyridine salts, picoline salts, quinoline salts, and isoquinoline salts; quaternary ammonium salts such as tetramethylammonium salts, tetraethylammonium salt, benzyltrimethylammonium salts, benzyltriethylammonium salts, benzyltributylammonium salts, methyltrioctylammonium salts, and tetrabutylammonium salts; basic amino acid salts such as arginine salts and lysine salts; and the like.

Examples of pharmaceutically acceptable acidic salts of the compound of the invention include inorganic acid salts such as hydrochlorides, sulfates, nitrates, phosphates, carbonates, hydrogen carbonates, and perchlorates; organic acid salts such as acetates, propionates, lactates, maleates, fumarates, tartrates, malates, citrates, and ascorbate; sulfonates such as methanesulfonates, isethionates, benzenesulfonates, and p-toluenesulfonates; acidic amino acids such as aspartates and glutamates; and the like.

As used herein, "solvate" refers to a solvate of the compound of the invention or a pharmaceutically acceptable salt thereof, encompassing, for example, a solvate of an organic solvent (e.g., alcohol (ethanol or the like)-ate), hydrate, and the like. When forming a hydrate, this can be coordinated with any number of water molecules. Examples of hydrates include monohydrates, dihydrates, and the like.

As used herein, "iFECD" (immobilized Fuchs' endothelial corneal dystrophy) is an abbreviation for immortalized cells in Fuchs' endothelial corneal dystrophy.

As used herein, "HCFC" is an abbreviation for human corneal endothelial cells. In addition, "iHCEC" is an abbreviation for immortalized human corneal endothelial cells.

As used herein, a "subject" refers to a target of administration (transplant) of a therapeutic or preventive medicament or method of the invention. Examples of subjects include mammals (e.g., human, mouse, rat, hamster, rabbit, cat, dog, cow, horse, sheep, monkey, and the like), but primates are preferable and humans are particularly preferable.

As used herein, "corneal endothelial condition, disorder, or disease" refers to any condition, disorder, or disease associated with the corneal endothelium. Representative examples thereof include, but are not limited to, Fuchs' endothelial corneal dystrophy, corneal guttata, post-corneal transplant disorder, corneal endotheliitis, trauma, post-ophthalmic surgery disorder, post-ophthalmic laser surgery disorder, aging, posterior polymorphous dystrophy (PPD), congenital hereditary endothelial dystrophy (CHED), idiopathic corneal endothelial disorder, cytomegalovirus corneal endotheliitis, and the like. In a preferred embodiment, a corneal endothelial condition, disorder, or disease comprises Fuchs' endothelial corneal dystrophy. In another embodiment, a corneal endothelial condition, disorder, or disease is due to overexpression of extracellular matrix (ECM), e.g., due to overexpression of type I collagen, type IV collagen, type V collagen, and fibronectin.

A corneal endothelial condition, disorder, or disease due to overexpression of extracellular matrix (ECM) includes any condition, disorder, or disease with overexpression of ECM observed in the corneal endothelium. Examples thereof include, but are not limited to, Fuchs' endothelial corneal dystrophy, guttae formation, thickening of a Descemet's membrane, thickening of a cornea, corneal opacity, scar, corneal nebula, corneal macula, leukoma, glare, blurred vision, and the like.

(General Technology)

The molecular biological methodology, biochemical methodology, and microbiological methodology used herein are well known and conventionally used in the art, which are described, for example, in Sambrook J. et al. (1989). Molecular Cloning: A Laboratory Manual, Cold Spring Harbor and 3rd Ed. thereof (2001); Ausubel, F. M. (1987). Current Protocols in Molecular Biology, Greene Pub. Associates and Wiley-Interscience; Ausubel, F. M. (1989). Short Protocols in Molecular Biology: A Compendium of Methods from Current Protocols in Molecular Biology, Greene Pub. Associates and Wiley-Interscience; Innis, M. A. (1990). PCR Protocols: A Guide to Methods and Applications, Academic Press; Ausubel, F. M. (1992). Short Protocols in Molecular Biology: A Compendium of Methods from Current Protocols in Molecular Biology, Greene Pub. Associates; Ausubel, F. M. (1995). Short Protocols in Molecular Biology: A Compendium of Methods from Current Protocols in Molecular Biology, Greene Pub. Associates; Innis, M. A. et al. (1995). PCR Strategies, Academic Press; Ausubel, F. M. (1999). Short Protocols in Molecular Biology: A Compendium of Methods from Current Protocols in Molecular Biology, Wiley, and annual updates; Sninsky, J. J. et al. (1999). PCR Applications: Protocols for Functional Genomics, Academic Press, Gait, M. J. (1985). Oligonucleotide Synthesis: A Practical Approach, IRL Press; Gait, M. J. (1990). Oligonucleotide Synthesis: A Practical Approach, IRL Press; Eckstein, F. (1991). Oligonucleotides and Analogues: A Practical Approach, IRL Press; Adams, R. L. et al. (1992). The Biochemistry of the Nucleic Acids, Chapman & Hall; Shabarova, Z. et al. (1994). Advanced Organic Chemistry of Nucleic Acids, Weinheim; Blackburn, G. M. et al. (1996). Nucleic Acids in Chemistry and Biology, Oxford University Press; Hermanson, G. T. (1996). Bioconjugate Techniques, Academic Press, Bessatsu Jikken Igaku [*Experimental Medicine, Supplemental Volume*], Idenshi Donyu & Hatsugen Kaiseki Jikken Ho [*Experimental Methods for Transgenesis & Expression Analysis*], Yodosha, 1997, or the like. The reports by Nancy Joyce et al. {Joyce, 2004 #161} and {Joyce, 2003 #7} are well known for corneal endothelial cells. However, as described above, long-term culture or subculture results in fibroblast-like transformation, and research for an effective culturing method are currently ongoing. Relevant portions thereof (which may be the entire document) are incorporated herein by reference.

DESCRIPTION OF PREFERRED EMBODIMENTS

The preferred embodiments are described hereinafter. It is understood that the embodiments are exemplification of the present invention, so that the scope of the present invention is not limited to such preferred embodiments. It should be understood that those skilled in the art can refer to the following preferred embodiments to readily make modifications or changes within the scope of the present invention. Any of these embodiments can be appropriately combined by those skilled in the art.

<Composition>

In one aspect, the present invention provides a composition for treating or preventing a corneal endothelial condition, disorder, or disease, comprising (T)EW-7197 (N-((4-([1,2,4]triazolo[1,5-a]pyridin-6-yl)-5-(6-methylpyridin-2-yl)-1H-imidazol-2-yl)methyl)-2-fluoroaniline) or a derivative thereof, or a pharmaceutically acceptable salt thereof, or a solvate thereof. In some embodiments, the composition of the invention is for suppressing a reduction in a corneal endothelial cell density. (T)EW-7197 used in the composition of the invention can suppress corneal endothelial disorders in the same manner as SB431542 that is known to suppress corneal endothelial disorders. Surprisingly, the effect of suppressing corneal endothelial disorders of (T)EW-7197 is also observed at very low concentrations. While an effect of suppressing corneal endothelial disorders was not observed for SB431542 at sub-µM (1 µM to 0.1 µM), a very potent effect of suppressing corneal endothelial disorders was observed for (T)EW-7197 even at a low concentration of 0.03 µM. In this manner, (T)EW-7197 used in the present invention can exert a very high therapeutic effect in the corneal endothelium. Further, toxicity to cells was hardly found in a cell survival rate test, so that (T)EW-7197 is also excellent in terms of safety.

In another aspect, the present invention provides a composition for suppressing a reduction in a corneal endothelial cell density, comprising (T)EW-7197 (N-((4-([1,2,4]triazolo[1,5-a]pyridin-6-yl)-5-(6-methylpyridin-2-yl)-1H-imidazol-2-yl)methyl)-2-fluoroaniline) or a derivative thereof, or a pharmaceutically acceptable salt thereof, or a solvate thereof.

In another aspect, the present invention provides (T)EW-7197 (N-((4-([1,2,4]triazolo[1,5-a]pyridin-6-yl)-5-(6-methylpyridin-2-yl)-1H-imidazol-2-yl)methyl)-2-fluoroaniline) or a derivative thereof, or a pharmaceutically acceptable salt thereof, or a solvate thereof (hereinafter, referred to as the compound of the invention or the like) for treating or preventing a corneal endothelial condition, disorder, or disease. In some embodiments, the compound of the invention or the like is for suppressing a reduction in a corneal endothelial cell density. (T)EW-7197 in the compound of the invention or the like can suppress corneal endothelial disorders in the same manner as SB431542 that is known to suppress corneal endothelial disorders. Surprisingly, the effect of suppressing corneal endothelial disorders of (T)EW-7197 is also observed at very low concentrations. While an effect of suppressing corneal endothelial disorders was not observed for SB431542 at sub-µM (1 µM to 0.1 µM), a very potent effect of suppressing corneal endothelial disorders was observed for (T)EW-7197 even at a low concentration of 0.03 µM. In this manner, (T)EW-7197 used in the present invention can exert a very high therapeutic effect in the corneal endothelium. Further, toxicity to cells was hardly found in a cell survival rate test, so that (T)EW-7197 is also excellent in terms of safety.

The composition of the invention can be a pharmaceutical composition (e.g., eye drop, intracameral injection, intravitreal injection, or subconjunctival injection). A pharmaceutical composition can further comprise a pharmaceutically acceptable carrier. Examples of pharmaceutically acceptable carriers include, but are not limited to, any solvent, diluting agent, other liquid vehicles, dispersion or suspension promoters, surface activators, isotonizing agents, thickeners, emulsifiers, preservatives, solid binding agents, lubricants, and the like that would be suitable for a specific desired dosage form. Remington's Pharmaceutical Sciences, Edited by Gennaro, Mack Publishing, Easton, PA, 1995 discloses various carriers used in known technologies for formulation of pharmaceutical compositions and the preparation thereof. Some examples of materials that can function as a pharmaceutically acceptable carrier include, but are not limited to, sugars such as lactose, glucose, and sucrose; starches such as corn starch and potato starch; cellulose and derivatives thereof such as carboxymethylcellulose sodium, ethyl cellulose, and cellulose acetate; powdered tragacanth; malt; gelatin; talc; excipients such as cocoa powder and suppository wax; oil such as peanut oil, cotton seed oil, safflower oil, sesame oil, olive oil, corn oil, and soybean oil; glycols such as propylene glycol; esters such as ethyl oleate and ethyl laureate; agar; buffering agents such as magnesium hydroxide and aluminum hydroxide; alginic acid; pyogenic substance-free water; isotonic saline; Ringer's solution; ethyl alcohol, and phosphate buffered solution. Other nontoxic and compatible lubricants such as sodium lauryl sulfate and magnesium stearate, as well as a colorant, releasing agent, coating agent, sweetener, flavoring agent, fragrance, preservative, and antioxidant can also be in the composition in accordance with the judgement of the preparer.

In one embodiment, the composition of the invention can treat or prevent a corneal endothelial condition, disorder, or disease due to a reduction in a corneal endothelial cell density. A corneal endothelial condition, disorder, or disease due to a reduction in a corneal endothelial cell density is selected from the group consisting of Fuchs' corneal endothelial dystrophy, cornea guttata, posterior polymorphous dystrophy, iridocorneal endothelial syndrome, congenital hereditary endothelial dystrophy, viral disease (cytomegalovirus corneal endotheliitis or herpes simplex virus corneal endotheliitis), exfoliation syndrome, post-corneal transplant rejection, bullous keratopathy, post-corneal transplant disorder, corneal endotheliitis, trauma, ophthalmic surgery or post-ophthalmic laser surgery disorder, or aging.

In one embodiment, a corneal endothelial condition, disorder, or disease is selected from the group consisting of Fuchs' endothelial corneal dystrophy, corneal guttata, post-corneal transplant disorder, corneal endotheliitis, trauma, post-ophthalmic surgery disorder, post-ophthalmic laser surgery disorder, aging, posterior polymorphous dystrophy (PPD), congenital hereditary endothelial dystrophy (CHED), idiopathic corneal endothelial disorder, and cytomegalovirus corneal endotheliitis. In another embodiment, a corneal endothelial condition, disorder, or disease is Fuchs' endothelial corneal dystrophy or corneal guttata.

In another aspect, the present invention provides a composition for treating or preventing a corneal endothelial condition, disorder, or disease due to overexpression of extracellular matrix (ECM), comprising (T)EW-7197 (N-((4-([1,2,4]triazolo[1,5-a]pyridin-6-yl)-5-(6-methylpyridin-2-yl)-1H-imidazol-2-yl)methyl)-2-fluoroaniline) or a derivative thereof, or a pharmaceutically acceptable salt thereof, or a solvate thereof. In another aspect, the present invention provides (T)EW-7197 (N-((4-([1,2,4]triazolo[1,5-a]pyridin-6-yl)-5-(6-methylpyridin-2-yl)-1H-imidazol-2-yl)methyl)-2-fluoroaniline) or a derivative thereof, or a pharmaceutically acceptable salt thereof, or a solvate thereof (hereinafter, also referred to as the compound of the invention or the like) for treating or preventing a corneal endothelial condition, disorder, or disease due to overexpression of extracellular matrix (ECM). (T)EW-7197 can unexpectedly suppress an abnormality (e.g., overexpression) of extracellular matrix (ECM) such as fibronectin in corneal endothelial cells. For example, an abnormality (e.g., overexpression) of extracellular matrix (ECM) such as type I collagen, type IV collagen, or type V collagen is also confirmed in Fuchs' endothelial corneal dystrophy. The composition of the invention or the compound of the invention or the like can also suppress abnormalities in such extracellular matrices (ECM). Examples of corneal endothelial condition, disorder, or disease due to overexpression of extracellular matrix (ECM) include Fuchs' endothelial corneal dystrophy, guttae formation, thickening of a Descemet's membrane, thickening of a cornea, corneal opacity, scar, corneal nebula, corneal macula, leukoma, glare, blurred vision, and the like. Fuchs' endothelial corneal dystrophy is a disease in which the density of corneal endothelial cells significantly decreases, and extracellular matrix is deposited on the Descemet's membrane, resulting in corneal guttae and thickening of the Descemet's membrane. For this reason, suppression of the overexpression of extracellular matrix means that significant improvement, and in some cases, complete healing is possible in treating or preventing Fuchs' endothelial corneal dystrophy. It is also possible to improve, treat, or prevent corneal guttae and thickening of the Descemet's membrane, as well as other conditions associated with turbidity or deposition (irreversible turbidity in corneal stroma due to protracted corneal edema or the like) that can occur due to overproduction of extracellular matrix in corneal endothelial disorders such as Fuchs' endothelial corneal dystrophy. Furthermore, overexpression of a proteoglycan such as agrin is also confirmed in Fuchs' endothelial corneal dystrophy. Overexpression of a proteoglycan such as agrin can result in corneal guttae and thickening of the Descemet's membrane, as well as other conditions associated with turbidity or deposition described above. The composition of the invention or the compound of the invention or the like can also suppress overexpression of a proteoglycan such as agrin.

In one embodiment, examples of the utilization method of the invention include, but are not limited to, eye drops. Other examples thereof include dosage modes (administration methods and dosage forms) such as eye ointment, intracameral injection, impregnation into a sustained release agent, subconjunctival injection, systemic administration (oral administration, intravenous injection), and the like.

The concentration of (T)EW-7197 used in the present invention is generally 0.001 to about 100 µM (µmol/1), preferably about 0.01 to about 30 µM, more preferably about 0.03 to about 10 µM, and still more preferably about 0.03 to about 1 µM. Examples of other concentration ranges include, but are not limited to, generally about 0.01 nM to about 100 µM, about 0.1 nM to about 100 µM, about 0.001 to about 100 µM, about 0.01 to about 75 µM, about 0.05 to about 50 µM, about 1 to about 10 µM, about 0.01 to about 10 µM, about 0.05 to about 10 µM, about 0.075 to about 10 µM, about 0.1 to about 10 µM, about 0.5 to about 10 µM, about 0.75 to about 10 µM, about 1.0 to about 10 µM, about 1.25 to about 10 µM, about 1.5 to about 10 µM, about 1.75 to about 10 µM, about 2.0 to about 10 µM, about 2.5 to about 10 µM, about 3.0 to about 10 µM, about 4.0 to about 10 µM, about 5.0 to about 10 µM, about 6.0 to about 10 µM, about 7.0 to about 10 µM, about 8.0 to about 10 µM, about 9.0 to about 10 µM, about 0.01 to about 50 µM, about 0.05 to about 5.0 µM, about 0.075 to about 5.0 µM, about 0.1 to about 5.0 µM, about 0.5 to about 5.0 µM, about 0.75 to about 5.0 µM, about 1.0 to about 5.0 µM, about 1.25 to about 5.0 µM, about 1.5 to about 5.0 µM, about 1.75 to about 5.0 µM, about 2.0 to about 5.0 µM, about 2.5 to about 5.0 µM, about 3.0 to about 5.0 µM, about 4.0 to about 5.0 µM, about 0.01 to about 3.0 µM, about 0.05 to about 3.0 µM, about 0.075 to about 3.0 µM, about 0.1 to about 3.0 µM, about 0.5 to about 3.0 µM, about 0.75 to about 3.0 µM, about 1.0 to about 3.0 µM, about 1.25 to about 3.0 µM, about 1.5 to about 3.0 µM, about 1.75 to about 3.0 µM, about 2.0 to about 3.0 µM, about 0.01 to about 1.0 µM, about 0.05 to about 1.0 µM, about 0.075 to about 1.0 µM, about 0.1 to about 1.0 µM, about 0.5 to about 1.0 µM, about 0.75 to about 1.0 µM, about 0.09 to about 35 µM, and about 0.09 to about 3.2 µM, more preferably about 0.01 to about 10 µM, about 0.1 to about 3 µM, and about 0.1 to about 1.0 µM.

When used as an eye drop, the formulation concentration can be determined with about 1 to 10000-fold, preferably about 100 to 10000-fold such as about 1000-fold of the effective concentration described above as the baseline while taking dilution with lacrimal fluid into account and being mindful of toxicity. The concentration can be set to a concentration exceeding such concentrations. Examples thereof include about 0.01 µM (µmol/1) to about 1000 mM (mmol/1), about 0.03 µM to about 1000 mM, about 0.1 µM to about 100 mM, about 0.3 µM to about 100 mM, about 1 µM to about 100 mM, about 3 µM to about 100 mM, about 10 µM to about 100 mM, about 30 µM to about 100 mM, about 0.1 µM to about 30 mM, about 0.3 µM to about 30 mM, about 1 µM to about 30 mM, about 3 µM to about 30 mM, about 1 µM to about 10 mM, about 3 µM to about 10 mM, about 10 µM to about 1 mM, about 30 µM to about 1 mM, about 10 µM to about 10 mM, about 30 µM to about 10 mM, about 100 µM to about 10 mM, about 300 µM to about 10 mM, about 10 µM to about 100 mM, about 30 µM to about 100 mM, about 100 µM to about 100 mM, about 300 µM to about 100 mM, about 1 mM to about 10 mM, about 1 mM to about 50 mM, and about 1 mM to about 100 mM. These upper limits the lower limits can be appropriately combined and determined.

In one embodiment, (T)EW-7197 or a derivative thereof, or a pharmaceutically acceptable salt thereof, or a solvate thereof can be present in the composition at a concentration of about 0.03 µM to about 10 µM and preferably about 0.03 µM to about 1 µM.

In yet another embodiment, the composition of the invention is provided as an eye drop, wherein (T)EW-7197 or a derivative thereof, or a pharmaceutically acceptable salt thereof, or a solvate thereof can be present at about 0.03 mM to about 100 mM, preferably about 0.001 mM to about 10 mM, more preferably about 0.05 mM to about 10 mM, still more preferably about 0.01 mM to about 5 mM, and most preferably about 0.1 mM to about 5 mM. In a specific embodiment, the composition of the invention provided as an eye drop can comprise about 0.5 mM of (T)EW-7197 or a derivative thereof, or a pharmaceutically acceptable salt thereof, or a solvate thereof.

The effective dose of the medicament of the invention that is effective for treating a specific disease, disorder, or condition can vary depending on the nature of the disorder or condition, but can be determined by those skilled in the art with standard clinical technology based on the description herein. Furthermore, an in vitro assay can be used to assist in the identification of the range of optimal dosages as needed. Since the accurate dose to be used in a combined agent can also vary depending on the route of administration and the severity of the disease or disorder, the dose should be determined in accordance with the judgment of a physician or the status of each patient. However, the dosage, although not particularly limited, can be, for example 0.001, 1, 5, 10, 15, 100, or 1000 mg/kg body weight per dosing or a value within the range of any two of said values. The dosing interval is not particularly limited, but can be, for example, 1 or 2 administrations per 1, 7, 14, 21, or 28 days, or 1 or 2 administrations per days within the range of any two of them. The dosage, number of dosing, dosing interval, dosing period, and dosing method can be appropriately selected depending on the patient's age or body weight, condition, dosing mode, target organ, or the like. For example, the present invention can be used as an eye drop. Further, the medicament of the invention can be injected into the anterior chamber. Further, a therapeutic drug preferably comprises an active ingredient at a therapeutically effective amount, or at an amount effective to exert a desired action. When a therapeutic marker significantly decreases after administration, it can be determined that a therapeutic effect was exerted. An effective dose can be estimated from a dose-response curve obtained from an in vitro or animal model testing system.

<Therapeutic or Preventive Method>

In one aspect, the present invention is a method of treating or preventing a corneal endothelial condition, disorder, or disease in a subject, comprising administering to the subject an effective amount of (T)EW-7197 (N-((4-([1,2,4]triazolo[1,5-a]pyridin-6-yl)-5-(6-methylpyridin-2-yl)-1H-imidazol-2-yl)methyl)-2-fluoroaniline) or a derivative thereof, or a pharmaceutically acceptable salt thereof, or a solvate thereof. One or more of the embodiments described above in <Composition> herein or the like can be appropriately employed in the method of the invention.

In yet another aspect, the present invention is a method of treating or preventing a corneal endothelial condition, disorder, or disease due to overexpression of extracellular matrix (ECM), comprising administering to the subject an effective amount of (T)EW-7197 (N-((4-([1,2,4]triazolo[1,5-a]pyridin-6-yl)-5-(6-methylpyridin-2-yl)-1H-imidazol-2-yl)methyl)-2-fluoroaniline) or a derivative thereof, or a pharmaceutically acceptable salt thereof, or a solvate thereof. One or more of the embodiments described above in <Composition> herein or the like can be appropriately employed in the method of the invention.

<Use>

In one aspect, the present invention provides use of (T)EW-7197 (N-((4-([1,2,4]triazolo[1,5-a]pyridin-6-yl)-5-(6-methylpyridin-2-yl)-1H-imidazol-2-yl)methyl)-2-fluoroaniline) or a derivative thereof, or a pharmaceutically acceptable salt thereof, or a solvate thereof in the manufacture of a medicament for treating or preventing a corneal endothelial condition, disorder, or disease. One or more of the embodiments described above in <Composition> herein or the like can be appropriately employed in the use of the invention.

In yet another aspect, the present invention provides use of (T)EW-7197 (N-((4-([1,2,4]triazolo[1,5-a]pyridin-6-yl)-5-(6-methylpyridin-2-yl)-1H-imidazol-2-yl)methyl)-2-fluoroaniline) or a derivative thereof, or a pharmaceutically acceptable salt thereof, or a solvate thereof in the manufacture of a medicament for treating or preventing a corneal endothelial condition, disorder, or disease due to overexpression of extracellular matrix (ECM). One or more of the embodiments described above in <Composition> herein or the like can be appropriately employed in the use of the invention.

<Composition for Preservation and Preservation Method>

In another aspect, the present invention provides a composition for preserving a corneal endothelial cell, comprising (T)EW-7197 or a derivative thereof, or a pharmaceutically acceptable salt thereof, or a solvate thereof. In a preferred embodiment, preservation is cryopreservation. It is understood that the (T)EW-7197 used in the present invention can be used in any form described herein, such as a form that is suitable as a composition for preservation among the embodiments described as a medicament. As used herein, "composition for preservation" is a composition for preserving a corneal fragment extracted from a donor for a period until the fragment is transplanted into a recipient, or for preserving a corneal endothelial cell before growth, or grown corneal endothelial cell.

In one aspect, the present invention provides use of (T)EW-7197 or a derivative thereof, or a pharmaceutically acceptable salt thereof, or a solvate thereof in the manufacture of a composition for preservation of a corneal endothelial cell. In another aspect, the present invention provides (T)EW-7197 or a derivative thereof, or a pharmaceutically acceptable salt thereof, or a solvate thereof for use in preservation of a corneal endothelial cell. In yet another aspect, the present invention provides a method of preserving a corneal endothelial cell, comprising preserving using a composition for preservation of a corneal endothelial cell comprising (T)EW-7197 or a derivative thereof, or a pharmaceutically acceptable salt thereof, or a solvate thereof.

In one embodiment, the composition for preservation of the invention can be prepared by adding the (T)EW-7197 of the invention to a conventionally used preservation agent or preservation solution. Examples of such a cornea preservation solution include preservation solutions that are commonly used for corneal transplant (sclerocornea fragment preservation solution (Optisol GS®) or eye ball preservation solution for corneal transplant (EPII®), saline, phosphate-buffered saline (PBS), and the like.

The composition for preservation of the invention is used for preserving a cornea that is used in organ transplant or the like. The composition for preservation of the invention is also used as a preservation solution for cryopreserving corneal endothelial cells or as a component thereof.

In another embodiment of the composition for preservation of the invention used for cryopreservation, an existing cryopreservation solution can be used by adding a composition for preservation comprising (T)EW-7197 or a derivative thereof, or a pharmaceutically acceptable salt thereof, or a solvate thereof of the invention. Examples of a cryopreservation solution include, but are not limited to, CELL-BANKER® series provided by Takara Bio (CELL BANKER PLUS (catalog number: CB021), CELL BANKER 2 (catalog number: CB031), STEM-CELL-BANKER (catalog number: CB043) and the like), KM BANKER (Kohjin Bio, catalog number: KOJ-16092005), and Freezing Medium, Animal Component Free, CRYO Defined (also denoted as Cnt-CRYO) (CELLNTEC, catalog number: CnT-CRYO-50). In yet another embodiment, the cryopreservation solution used may be KM BANKER. It is understood that those skilled in the art can use a suitable modified cryopreservation solution by appropriately changing a constituent component of the cryopreservation solution described above or by adding an additional constituent component. Glycerol, dimethyl sulfoxide, propylene glycol, acetamide, or the like may be further added to the preservation solution of the invention for cryopreservation.

Reference literatures such as scientific literatures, patents, and patent applications cited herein are incorporated herein by reference to the same extent that the entirety of each document is specifically described.

As described above, the present invention has been described while showing preferred embodiments to facilitate understanding. The present invention is described hereinafter based on the Examples. The aforementioned descriptions and the following Examples are not provided to limit the present invention, but for the sole purpose of exemplification. Thus, the scope of the present invention is not limited to the embodiments and Examples specifically described herein and is limited only by the scope of claims.

EXAMPLES

Hereinafter, examples of the present invention are described. Biological samples or the like, where applicable, were handled in compliance with the standards enacted by the Ministry of Health, Labour and Welfare, Ministry of Education, Culture, Sports, Science and Technology, or the like and, where applicable, based on the Helsinki Declaration or ethical codes prepared based thereon. For the donation of eyes used for the study, consent was obtained from the next of kin of all deceased donors. The present study was approved by the ethics committee of the University of Erlangen-Nuremberg (Germany) and SightLife™ (Seattle, WA) eye bank or a corresponding body thereof.

Preparation Example: Production of Fuchs' Endothelial Corneal Dystrophy Patient Derived Immortalized Corneal Endothelial Cell Line (iFECD) Model In this example, an immortalized corneal endothelial cell line (iFECD) was produced from corneal endothelial cells from Fuchs' endothelial corneal dystrophy patients.

(Culture Method)

Corneal endothelial cells were mechanically peeled off with a basal membrane from a cornea for research purchased from a Seattle eye bank. After collagenase was used to detach and collect the corneal endothelial cell from the basal membrane, the cells were subjected to primary culture. For a medium, Opti-MEM I Reduced-Serum Medium, Liquid (INVITROGEN catalog number: 31985-070), to which 8% FBS (BIOWEST, catalog number: S1820-500), 200 mg/mL of $CaCl_2.2H_2O$ (SIGMA catalog number: C7902-500G), 0.08% of chondroitin sulfate (SIGMA catalog number: C9819-5G), 20 µg/mL of ascorbic acid (SIGMA catalog number: A4544-25G), 50 µg/mL of gentamicin (INVITROGEN catalog number: 15710-064), and 5 ng/mL of EGF (INVITROGEN catalog number: PHG0311) were added, and conditioned for a 3T3 feeder cell was used as a basal medium. Further, the cells were cultured in a basal medium to which SB431542 (1 µmol/L) and SB203580 (4-(4-fluorophenyl)-2-(4-methylsulfonylphenyl)-5(4-pyridyl) imidazole<4-[4-(4-fluorphenyl)-2-(4-methylsulfinylphenyl)-1H-imidazole-5-yl]pyridine) (1 µmol/L) were added (also referred to as "SB203580+SB431542+3T3 conditioned medium" herein).

(Method of Acquisition)

Corneal endothelial cells were obtained with an approval from an ethics committee and written consent from human patients who suffered from bullous keratopathy according to a clinical diagnosis of Fuchs' endothelial corneal dystrophy and underwent corneal endothelial transplant (Descemet's Membrane Endothelial Keratoplasty=DMEK). For DMEK, pathological corneal endothelial cells were mechanically peeled off with the basal membrane, i.e., the Descemet's membrane, and immersed in a cornea preservation solution Optisol-GS (Bausch & Lomb). Collagenase treatment was then applied to enzymatically collect the corneal endothelial cells, and the cells were cultured with a SB203580+SB431542+3T3 conditioned medium. For cultured corneal endothelial cells from a Fuchs' endothelial corneal dystrophy patient, SV40 large T antigen and hTERT gene were amplified by PCR and introduced into a lentiviral vector (pLenti6.3_V5-TOPO; Life Technologies Inc). The lentiviral vector was then used to infect 293T cells (RCB2202; Riken Bioresource Center, Ibaraki, Japan) with a transfection reagent (Fugene HD; Promega Corp., Madison, WI) and three types of helper plasmids (pLP1, pLP2, pLP/VSVG; Life Technologies Inc.). Culture supernatant comprising viruses was collected 48 hours after the infection. 5 µg/ml of polybrene was used and added to a culture solution of cultured corneal endothelial cells from a Fuchs' endothelial corneal dystrophy patient, and SV40 large T antigen and hTERT gene were introduced. Images of the immortalized corneal endothelial cell line (iFECD) from Fuchs' endothelial corneal dystrophy patients from a phase contrast microscope were studied. Cultured corneal endothelial cells from a research cornea imported from the Seattle eye bank were immortalized by the same method to produce an immortalized cell line of normal corneal endothelial cells (iHCEC) as a control. When images of the immortalized corneal endothelial cell line (iFECD) and the immortalized corneal endothelial cell line from a healthy donor (iHCEC) from a phase contrast microscope are studied, both iHCEC and iFECD have a layer of polygonal form as in normal corneal endothelial cells. iHCEC and iFECD were maintained and cultured with Dulbecco's modified Eagle medium (DMEM)+10% fetal bovine serum (FBS).

(Example of Observation with a Phase Contrast Microscope)

The medium was removed from a culture dish culturing immortalized human corneal endothelial cells from a Fuchs' endothelial corneal dystrophy patient (iFECD), and 1×PBS (−) preheated to 37° C. was added and washed. This was repeated twice. 1×PBS(−) was added again and the medium was incubated for 5 minutes at 37° C. (5% $CO_2$). After removing the PBS(−), 0.05% Trypsin-EDTA (Nacalai Tesque, 32778-34) was added and incubated for 5 minutes at 37° C. (5% $CO_2$). The medium was then suspended and centrifuged for 3 minutes at 1500 rpm to retrieve cells. DMEM (Nacalai Tesque, 08456-36)+10% FBS (Biowest, S1820-500)+1% P/S (Nacalai Tesque, 26252-94) was used as the medium.

The immortalized human corneal endothelial cells from a Fuchs' endothelial corneal dystrophy patient (iFECD) were seeded on a 12-well plate at a ratio of $8.0 \times 10^4$ cells per well and cultured for 24 hours at 37° C. (5% $CO_2$). DMEM+10% FBS+1% P/S was used as the medium.

After 24 hours, the medium was exchanged and cultured again for 24 hours. DMEM+2% FBS+1% P/S was used as the medium.

After 24 hours, the medium was removed. 10 ng/ml of Transforming Growth Factor-132 Human recombinant (WAKO, 200-19911) was added, and the medium was cultured for 24 hours. DMEM+2% FBS+1% P/S was used as the medium. After 24 hours, the cell morphology and apoptosis were observed under a phase contrast microscope.

Immortalized human corneal endothelial cells from a Fuchs' endothelial corneal dystrophy patient (iFECD) were impaired when the cells were stimulated with TGF-β, as shown in FIG. 1.

Example 1: Effect of Suppressing Corneal Endothelial Cell Disorder with EW-7197

In this Example, the effect of suppressing corneal endothelial cell disorders with EW-7197 was observed using immortalized human corneal endothelial cells from a Fuchs' endothelial corneal dystrophy patient (iFECD). The cells were observed by a method based on the observation example described above. SB431542 known to suppress corneal endothelial cell disorders was used as the target (see International Publication No. WO 2015/064768).

(Materials and Methods)

After iFECDs were seeded on a 12-well plate and cultured for 24 hours, the medium was removed. SB431542 (WAKO, 192-16541) and EW-7197 (Selleck Chemicals, 57530) were added so that the final concentration would each be 0.1, 0.3, 1, 3, or 10 µM, and the medium was cultured for 24 hours. DMEM+2% FBS+1% P/S was used as the medium.

After 24 hours, the medium was removed. 10 ng/ml of Transforming Growth Factor-β2 Human recombinant (WAKO, 200-19911) as well as SB431542 and EW-7197 were added so that the final concentration would each be 0.1, 0.3, 1, 3, or 10 µM, and the medium was cultured for 24 hours. DMEM+2% FBS+1% P/S was used as the medium.

After 24 hours, the cell morphology and apoptosis were observed under a phase contrast microscope.

(Results)

The results are shown in FIGS. 2 and 3. It was observed that when pretreated with SB431542, corneal endothelial cell disorder was suppressed at 3 µM and 10 µM, particularly at 10 µM, and corneal endothelial cell disorder was effectively suppressed, particularly at 10 µM. Meanwhile, it was observed that when pretreated with EW-7197, corneal endothelial cell disorder was effectively suppressed, particularly at 0.1, 0.3, and 1 µM. The effect of suppressing corneal endothelial cell disorder was also confirmed at 3 µM and 10 µM. It was surprisingly revealed that EW-7197 can suppress corneal endothelial cell disorders even at very low concentrations compared to SB431542 that has been known to be able to suppress corneal endothelial cell disorders.

Example 2: Study on the Concentration of EW-7197

This Example studied the concentration of EW-7197 at which an effect of suppressing corneal endothelial cell disorders is effectively observed. The effect of suppressing corneal endothelial cell disorders was observed through the same method as Example 1.

(Materials and Methods)

After iFECDs were seeded on a 12-well plate at a ratio of $7.0 \times 10^4$ cells and cultured for 24 hours, the medium was removed. EW-7197 (Selleck Chemicals, 57530) was added so that the final concentration would be 0.001, 0.003, 0.01, 0.03, 0.1, 0.3, 1, 3, 10, or 30 µM, and the medium was cultured for 24 hours. DMEM+2% FBS+1% P/S was used as the medium.

After 24 hours, the medium was removed. 10 ng/ml of Transforming Growth Factor-β2 Human recombinant (WAKO, 200-19911) and EW-7197 were added so that the final concentration would be 0.001, 0.003, 0.01, 0.03, 0.1, 0.3, 1, 3, 10, or 30 µM, and the medium was cultured for 24 hours. DMEM+2% FBS+1% P/S was used as the medium.

After 24 hours, the cell morphology and apoptosis were observed under a phase contrast microscope.

(Results)

Figure 4:
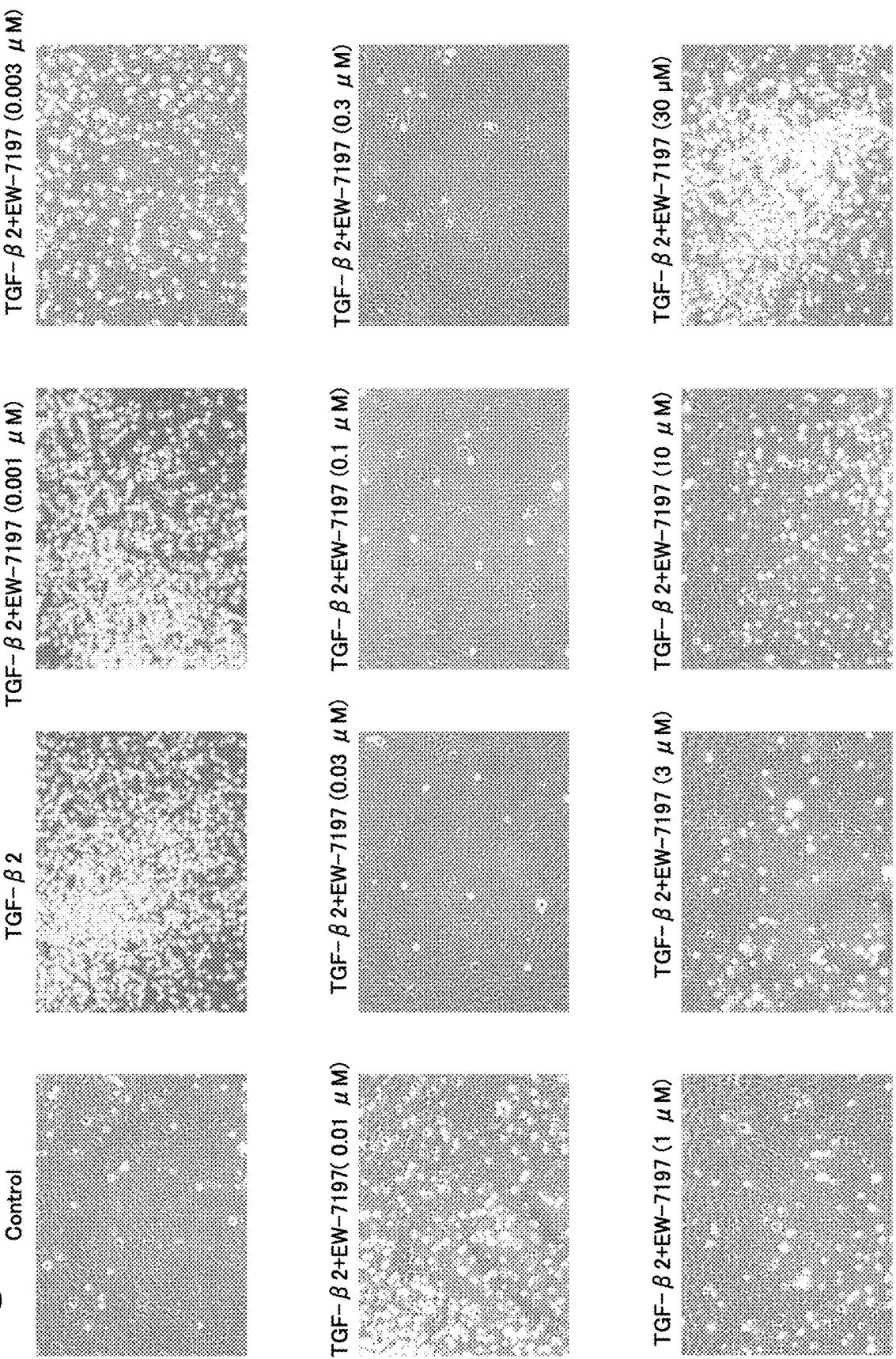
FIG. 4 shows phase contrast microscope pictures of immortalized corneal endothelial cells derived from a Fuchs' endothelial corneal dystrophy patient (iFECD) that were concentration-dependently treated with EW-7197.

The results are shown in FIG. 4. Significant cell damage was observed when immortalized human corneal endothelial cells from a Fuchs' endothelial corneal dystrophy patient (iFECD) were stimulated with TGF-β. In the EW-7197 added group, a particularly excellent effect of suppressing corneal endothelial cell disorders was observed, especially at 0.03, 0.1, 0.3, and 1 µM. It was also confirmed that corneal endothelial cell disorders were effectively suppressed at 3 µM and 10 µM. It was revealed in this manner that EW-7197 effectively suppresses corneal endothelial cell disorders in a wide concentration range.

Example 3: Cell Survival Rate and Caspase 3/7 Activity

This Example analyzed the cell survival rate and caspase 3/7 activity in the presence of EW-7197. SB431542 was used as a comparative control.

(Materials and Methods)

(Analysis of Cell Survival Rate)

iFECDs were seeded on a 96-well plate at a ratio of $3 \times 10^3$ cells per well, and cultured until reaching confluence at 37° C. (5% $CO_2$). DMEM+10% FBS+1% P/S was used as the medium.

After 24 hours, the medium was removed. SB431542 (WAKO, 192-16541) and EW-7197 (Selleck Chemicals, 57530) were added so that the final concentration would each be 0.01, 0.1, 1, or 10 µM, and the medium was cultured for 48 hours. DMEM+2% FBS+1% P/S was used as the medium.

After 24 hours, the cell morphology was observed under a phase contrast microscope.

After observation, the cell survival rate was analyzed using Cell Titer-Glo Luminescent Cell Viability Assay by the following procedures. The medium was discarded so that the amount would be 50 µl per well, and Cell Titer-Glo Luminescent Cell Viability Assay solution (Promega, G7572) was added at 50 µl/well so that the ratio to the medium would be 1:1. The process was hereinafter conducted without exposure to light. The mixture was mixed thoroughly using a shaker for 2 minutes at about 120 $min^{-1}$, and incubated for 10 minutes. After the incubation, 80 µl was transferred to an Assay plate (Corning, 3912, Assay plate 96 well, white polystyrene), and absorbance was measured using a GloMax-Multi Detection System (Promega, E7051).

(Analysis of Caspase 3/7)

iFECDs were seeded on a 96-well plate at a ratio of $3 \times 10^3$ cells per well, and cultured until reaching confluence at 37° C. (5% $CO_2$). DMEM+10% FBS+1% P/S was used as the medium.

After 24 hours, the medium was removed. SB431542 (WAKO, 192-16541) and EW-7197 (Selleck Chemicals, 57530) were added so that the final concentration would each be 0.01, 0.1, 1, or 10 µM, and the medium was cultured for 24 hours. DMEM+2% FBS+1% P/S was used as the medium.

After 24 hours, the medium was removed. 10 ng/ml of Transforming Growth Factor-β2 Human recombinant (WAKO, 200-19911) and SB431542 were added so that the final concentration would be 0.01, 0.1, 1, and 10 µM, and the medium was cultured for 24 hours. DMEM+2% FBS+1% P/S was used as the medium.

After 24 hours, the cell morphology was observed under a phase contrast microscope.

After observation, Caspase 3/7 activity was measured using Caspase-Glo 3/7 Assay by the following procedures. The medium was discarded so that the amount would be 50 µl per well, and a Caspase Glo 3/7 Assay Reagent (mixture of Caspase-Glo 3/7 Assay Buffer and Caspase-Glo 3/7 Assay Substrate) (Promega, G8091) solution was added at 50 µl/well so that the ratio thereof to the medium would be 1:1. The process was hereinafter conducted without exposure to light. The mixture was mixed thoroughly using a shaker for 2 minutes at about 120 $min^{-1}$, and incubated for 40 minutes at room temperature. After the incubation, 80 µl was transferred to an Assay plate (Corning, 3912, Assay plate 96 well, white polystyrene), and absorbance was measured using a GloMax-Multi Detection System (Promega, E7051).

A caspase inhibitor, i.e., 10µ MZ-VD-FMK (WAKO, 262-02061) was used as a positive control.

(Results)

(Analysis of Cell Survival Rate)

Figure 5:
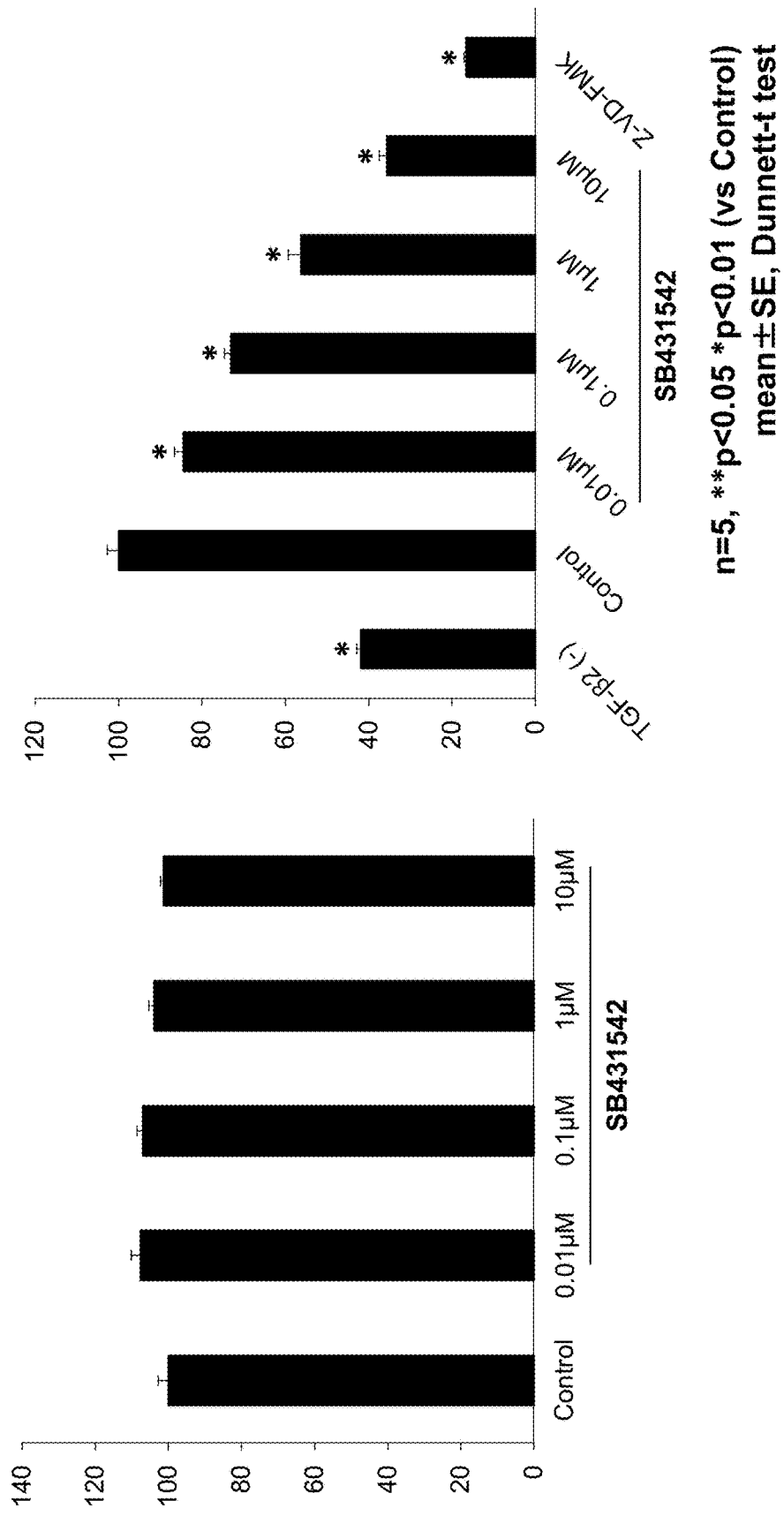
FIG. 5 shows graphs for cell survival rate and caspase 3/7 activity in iFECD in the presence of SB431542.
Figure 6:
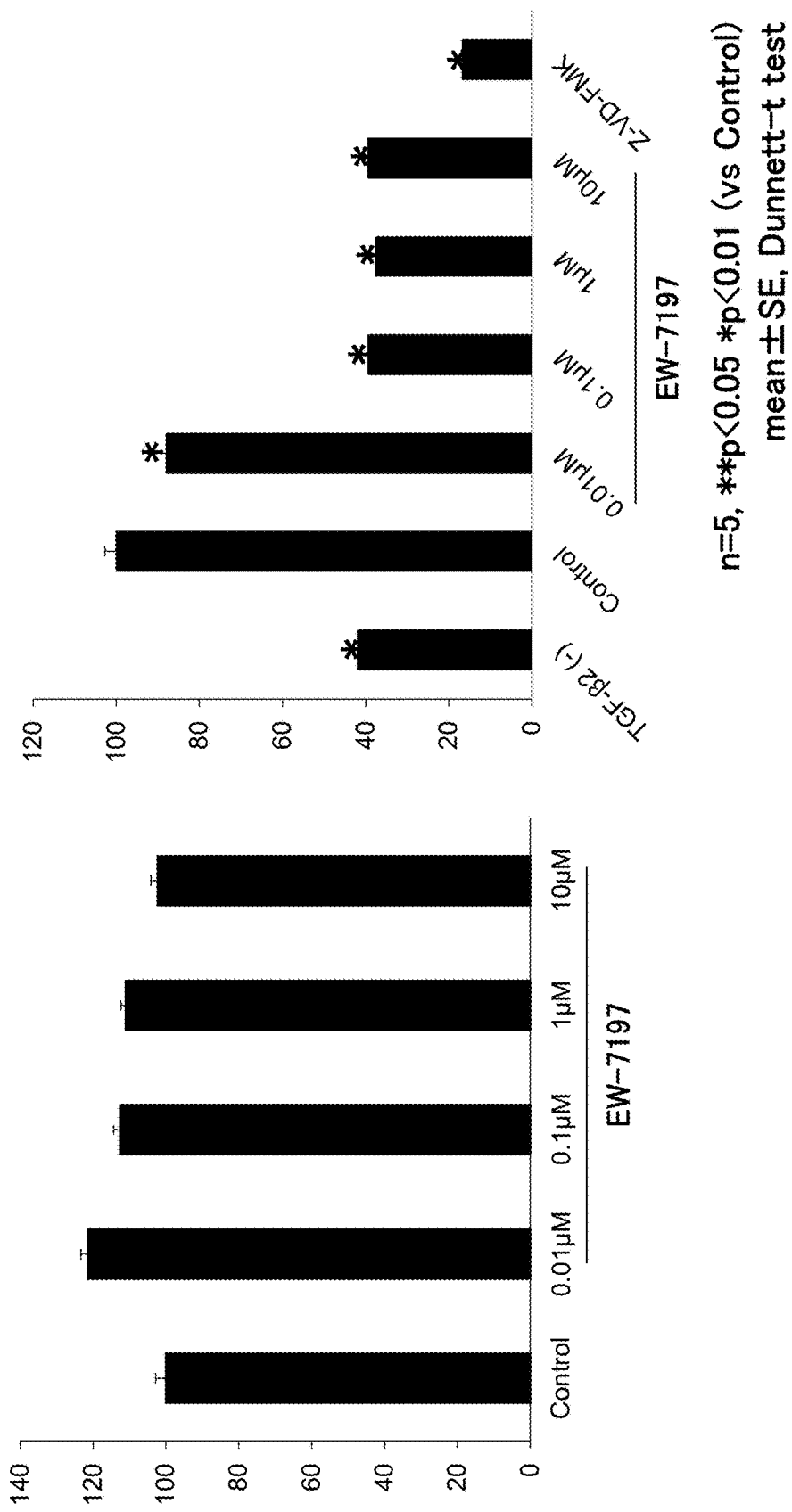
FIG. 6 shows graphs for cell survival rate and caspase 3/7 activity in iFECD in the presence of EW-7197.

The results are shown in FIGS. 5 and 6. As a result of measuring the cell survival rate using a Cell Titer-Glo Luminescent Cell Viability Assay, a significant difference was not found in the cell survival rate, when SB431542 was added, compared to a control group in all concentrations of 0.01, 0.1, 1, and 10 µM. In view of the above, addition of SB431542 does not result in a cell disorder at concentrations of 0.01, 0.1, 1, and 10 µM. Likewise, a significant difference was not found in the cell survival rate, when EW-7197 was added, compared to a control group in all concentrations of 0.01, 0.1, 1, and 10 µM. In view of the above, addition of EW-7197 does not result in a cell disorder at concentrations of 0.01, 0.1, 1, and 10 µM.

(Analysis of Caspase 3/7)

The results are shown in FIGS. 5 and 6. A Caspase-Glo 3/7 Assay can measure the activity of Caspase 3/7 associated with induction of apoptosis. Specifically, a higher activity of Caspase 3/7 indicates that a cell disorder is induced. It was found from FIG. 5 that when stimulated with TGF-β, Caspase 3/7 was significantly activated compared to no stimulation. Meanwhile, when SB431542 was added, activity of Caspase 3/7 was reduced, in the order of 0.01, 0.1, 1, and 10 µM. Particularly at 10 µM, the value was similar to that of a control group without stimulation with TGF-β. Accordingly, SB431542 inhibits the activity of Caspase 3/7 concentration dependently. The effect thereof is exhibited most effectively at 10 µM. When EW-7197 was added, Caspase 3/7 was inhibited significantly at 0.01 µM. The value was similar to that of the control group without simulation with TGF-β, especially at 0.1, 1, and 10 µM. It was revealed that EW-7197 can also inhibit Caspase 3/7 in the same manner as SB431542. In particular, a higher inhibitory effect was observed for EW-7197 compared to SB431542 even at 0.1 µM.

Example 4: Western Blot

This Example tested the expression of fibronectin (about 240 kDa), activated form of cleaved caspase 3 (about 17 kDa), and PARP (about 89 kDa) in iFECD upon addition of EW-7197 by Western blot.

(Materials and Methods)

iFECDs were seeded on a 12-well plate at a ratio of $8 \times 10^4$ cells per well, and cultured at 37° C. (5% $CO_2$) for 24 hours. DMEM+10% FBS+1% P/S was used as the medium.

After 24 hours, the medium was removed. EW-7197 (Selleck Chemicals, 57530) was added so that the final concentration would be 0.1, 1, or 10 µM, and SB431542 (WAKO, 192-16541) was added so that the final concentration would be 10 µM, and the medium was cultured for 24 hours. DMEM+2% FBS+1% P/S was used as the medium.

After 24 hours, the medium was removed and cultured for hours so that the final concentration of 10 ng/ml of Transforming Growth Factor-132 Human recombinant (WAKO, 200-19911) and EW-7917 would be 0.1, 1, and 10 µM, and that of SB431542 would be 10 µM. DMEM+2% FBS+1% P/S was used as the medium.

After 24 hours, the cell morphology and apoptosis were observed under a phase contrast microscope.

After the observation, Western blot was performed on proteins by the following procedures.

1) Retrieval of Protein

To retrieve floating and dead cells, the medium was retrieved on ice, cells were washed twice with 1×PBS(-) and the solution thereof was also retrieved. The solution was centrifuged for 5 min at 4° C. and 800 g and the supernatant was discarded to obtain a precipitate.

A protein extraction buffer (RIPA; 50 mM Tris-HCl (pH7.4), 150 mM NaCl, 1 mM EDTA, 0.1% SDS, 0.5% DOC, 1% NP-40) was added to the washed cells on ice to extract a protein.

Subsequently, the post-centrifugation precipitate of the floating and dead cells described above was also suspended and extracted together. The retrieved solution was pulverized three times for 30 seconds in cooled water with an ultrasound apparatus (BIORUPTOR, TOSHO DENKI) and then centrifuged for 10 minutes at 4° C. and 15000 rpm. The supernatant of the protein was retrieved.

2) Western Blotting

The extracted protein was separated by SDS-PAGE and transcribed onto a nitrocellulose membrane. The amount of protein was 4 µg for fibronectin, PARP, and GAPDH, and 10 µg for caspase 3. A mouse anti-Fibronectin antibody (BD Biosciences, 610077), rabbit anti-Caspase 3 antibody (Cell Signaling, 9662), rabbit anti-PARP antibody (Cell signaling, 9542), and mouse anti-GAPDH antibody (MBL, M171-3) were used as the primary antibody.

A peroxidase labeled anti-rabbit antibody and anti-mouse antibody (GE Healthcare Biosciences, NA931V, NA934V) were used as the secondary antibody. For the primary antibody, the mouse anti-Fibronectin antibody was diluted 20000-fold, rabbit anti-PARP antibody was diluted 1000-fold, rabbit anti-Caspase 3 antibody was diluted 1000-fold, and mouse anti-GAPDH antibody was diluted 3000-fold. All secondary antibodies were diluted 5000-fold. Chemi Lumi ONE Ultra (Nacalai Tesque, 11644-40) was used for the detection. The detected band intensities were analyzed with Lumino Image Analyzer LAS-4000 mini (Fuji Film) and ImageQuant™ software (GE Healthcare).

(Results)

Figure 7:
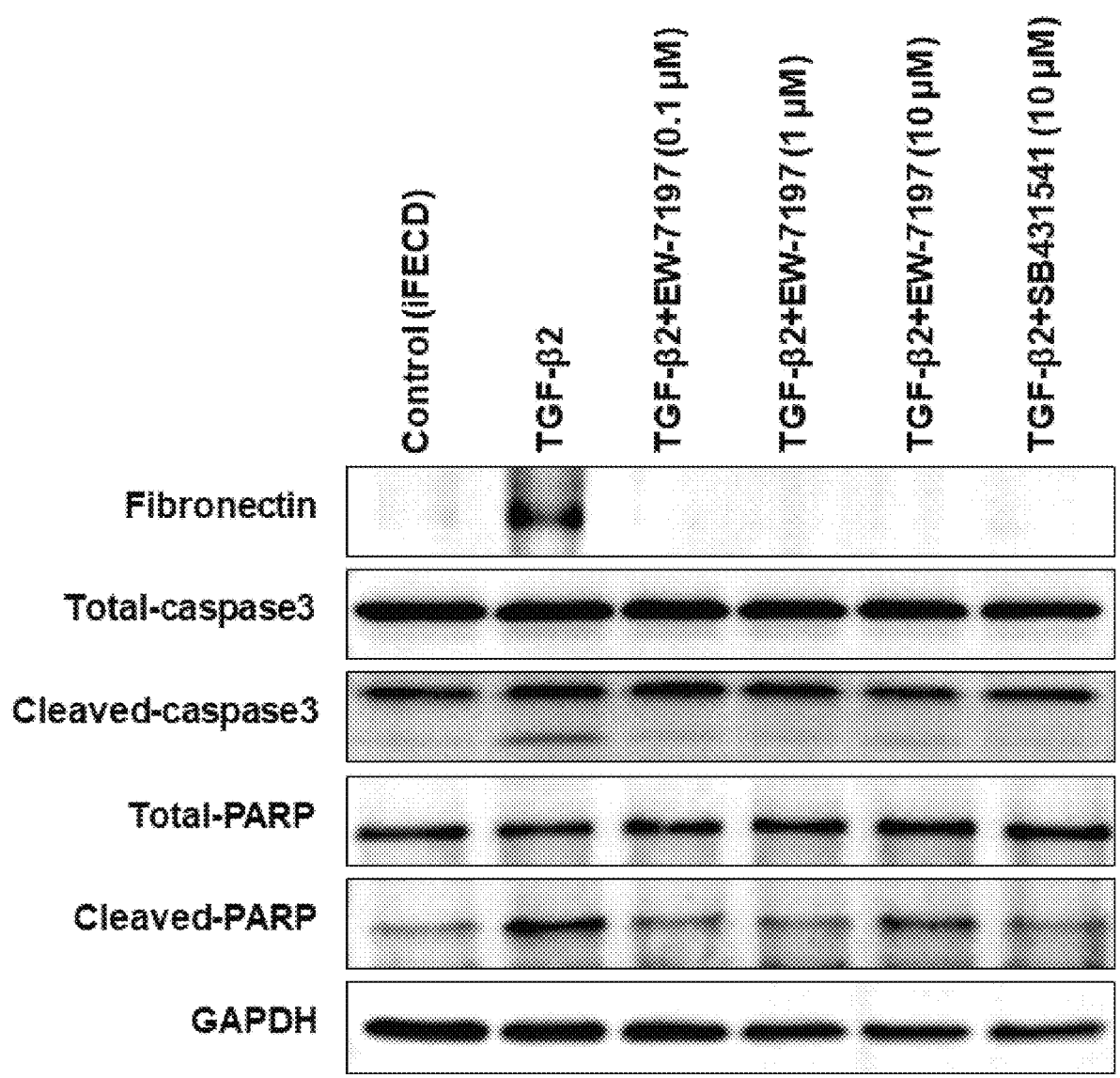
FIG. 7 shows results of Western blot for fibronectin, cleaved caspase 3, and PARP in iFECD.

The results are shown in FIG. 7. When iFECD was stimulated with TGF-β, expression of fibronectin (about 240 kDa), activated form of cleaved caspase 3 (about 17 kDa) and PARP (about 89 kDa) was observed. Meanwhile, expression of fibronectin was suppressed to the same degree as the control group without stimulation with TGF-β or 10 µM of SB431542 at any of the concentrations in the presence of EW-7197. The activated form of cleaved caspase 3 and PARP activity was also suppressed to the same degree as the control group without stimulation with TGF-β or 10 µM of SB431542. Therefore, Western blot analysis revealed that EW-7197 suppresses expression of fibronectin in the same manner as SB431542.

Example 5: Evaluation of Drug Efficacy of EW-7197 Eye Drops on Fuchs' Endothelial Corneal Dystrophy Using Col8a2 Knock-in Mice This Example evaluated the efficacy of an EW-7197 eye drop on Fuchs' endothelial corneal dystrophy using a Fuchs' endothelial corneal dystrophy animal model, Col8a2 knock-in mice. Col8a2 knock-in mice are established animal models of Fuchs' endothelial corneal dystrophy (reference: Jun et al., Hum Mol Genet. 2012 Jan. 15; 21(2): 384-93).

5 µL of 0.02% (about 0.5 mM) EW-7197 eye drop or a base agent (7% DMSO containing PBS) was administered as an eye drop to both eyes of 4-month-old alpha 2 collagen 8 gene (Col8a2) knock-in mice 4 times a day for 8 weeks. The corneal endothelial cell density was measured using a specular microscope KS3M (Konan Medical, Inc.) at before eye drops, and 2, 4, 6, and 8 weeks after eye drops. Mice were euthanized by intraperitoneally administering an excessive amount (200 mg/kg body weight or greater) of anesthetic injection Somnopentyl (Kyoritsu Seiyaku Corporation) 8 weeks after injection. After confirming cardiac arrest, both eye balls were harvested. The harvested eye balls were incised to prepare a corneal fragment. Immunostaining of type I collagen and fibronectin was performed as follows. Image-Pro (Nippon Roper K.K.) was used to analyze the area of type I collagen and fibronectin expression.

(Immunostaining Method of Type I Collagen and Fibronectin)

After immobilizing a mouse corneal fragment for 10 minutes at room temperature in 4% paraformaldehyde, 0.5% TritonX-100 was added and allowed to permeate for 5 minutes. 1% bovine serum albumin (BSA) was added and the fragment was incubated for 1 hour at room temperature. The corneal fragment was then immersed in a primary antibody solution and reacted overnight at 4° C. 1:200 diluent of type I collagen polyclonal antibody (Rockland Immunochemicals) and 1:250 diluent of fibronectin polyclonal antibody (abcam) were used as the primary antibody. Next, the corneal fragment was immersed in a mixture of a secondary antibody solution and DAPI solution (Dojindo Laboratories) and reacted for 1 hour at room temperature away from light. 1:2000 diluent of Alexa Fluor® 488-labeled goat anti-rabbit IgG (Life Technologies) was used as the secondary antibody. 1:1000 diluent of DAPI solution was used. The corneal fragment was stretched and placed on a slide glass, and enclosed with a cover glass. The prepared specimen was observed using a confocal laser scanning microscope Olympus FV1000 FLUOVIEW (Olympus Corporation).

(Results)

Table 1 shows results for the amount of change in the corneal endothelial cell density from before eye drop application to after 4 weeks and 8 weeks from eye drops in Col8a2 knock-in mice (DECD (cells/mm$^2$)). A decrease in the corneal endothelial cell density of 51.5 cells/mm$^2$ was observed after 4 weeks, and a decrease in the corneal endothelial cell density of 123.6 cells/mm$^2$ was observed after 8 weeks in normal mice without introduction of a Col8a2 gene. A slight decrease in the corneal endothelial cell density in normal mice is understood to be a result of a decrease in corneal endothelial cells due to aging.

TABLE 1

Amount of change in the corneal endothelial cell density in Col8a2 knock-in mice ($\Delta$ECD (cells/mm$^2$))

| Week | 0 (Before eye drop) | 4 | 8 |
|---|---|---|---|
| Base agent | 0 | −227.667 | −401.889 |
| 0.02% TEW | 0 | −121.4 | −284.5 |

As is apparent from Table 1, a decrease in the corneal endothelial cell density in the 0.02% EW-7197 eye drop administration group was suppressed significantly compared to the group administered with the base agent. A significant increase in the expression of type I collagen and fibronectin was observed by immunostaining in Col8a2 knock-in mice. FIG. 8 shows results of analyzing the area of type I collagen and fibronectin expression. The expression of type I collagen and fibronectin had a decreasing trend in the 0.02% EW-7197 eye drop administration group compared to the base agent administered group.

In this manner, it was revealed that EW-7197 sufficiently migrated into the corneal endothelium and effectively suppressed a decrease in corneal endothelial cells (apoptosis of corneal endothelial cells and the like) and/or corneal endothelial disorders represented by overexpression of extracellular matrix (type I collagen, fibronectin and the like) by eye drops of EW-7197.

Example 6: Evaluation of Efficacy of EW-7197 Eye Drop of Various Concentrations on Fuchs' Endothelial Corneal Dystrophy Using Col8a2 Knock-in Mice This Example evaluated the efficacy of EW-7197 eye drop of various concentrations on Fuchs' endothelial corneal dystrophy using Col8a2 knock-in mice.

(Methods)

5 μL of 0.02% (about 0.5 mM) EW-7197 eye drop, 0.1% (about 2.5 mM) EW-7197 eye drop, or a base agent (DMSO containing phosphate buffer) was administered as an eye drop to both eyes of 4-month-old alpha 2 collagen 8 gene (Col8a2) knock-in mice 4 times a day for 12 weeks. A surfactant was added to the base agent as needed. Those skilled in the art can use an appropriate and suitable surfactant (Kenji Motose (1984). "Tenganzai" [Eye drops] Nanzando; International Pharmaceutical Excipients Council Japan (2016). "Iyakuhin Tenkabutsu Jiten" [*Pharmaceutical Excipient Encyclopedia*] Yakuji Nippo, Limited). The corneal endothelial cell density was measured using a specular microscope KS3M (Konan Medical, Inc.) at before eye drops, and 3, 6, 9, and 12 weeks after eye drops. Mice were euthanized by intraperitoneally administering an excessive amount (200 mg/kg body weight or greater) of anesthetic injection Somnopentyl (Kyoritsu Seiyaku Corporation) 12 weeks after injection. After confirming cardiac arrest, both eye balls were harvested. The harvested eye balls were incised to prepare a corneal fragment. Immunostaining of fibronectin was performed. The immunostaining method was the following. Image-Pro (Nippon Roper K.K.) was used to analyze the area of fibronectin expression.

(Immunostaining Method of Fibronectin)

After immobilizing a mouse corneal fragment for 10 minutes at room temperature in 4% paraformaldehyde, 0.5% TritonX-100 was added and allowed to permeate for 5 minutes. 1% bovine serum albumin (BSA) was added and the fragment was incubated for 1 hour at room temperature. The corneal fragment was then immersed in a primary antibody solution and reacted overnight at 4° C. 1:250 diluent of fibronectin polyclonal antibody (abcam) was used as the primary antibody. Next, the corneal fragment was immersed in a mixture of a secondary antibody solution and DAPI solution (Dojindo Laboratories) and reacted for 1 hour at room temperature away from light. 1:2000 diluent of Alexa Fluor® 488-labeled goat anti-rabbit IgG (Life Technologies) was used as the secondary antibody. 1:1000 diluent of DAPI solution was used. The corneal fragment was stretched and placed on a slide glass, and enclosed with a cover glass. The prepared specimen was observed using a confocal laser scanning microscope Olympus FV1000 FLUOVIEW (Olympus Corporation) or a confocal laser scanning microscope LSM880 (Carl Zeiss Microscopy Co., Ltd.). The center section, 6 o'clock direction, 9 o'clock direction (ear side), and 3 o'clock direction (nose side)

regions of the cornea were observed with a field of vision of 40× magnification or 100× magnification.

(Results)

A tendency for suppressing a decrease in corneal endothelial density at the center section of the corneal was observed in the EW-7197 eye drop group up to week 6, but a significant difference in the corneal endothelial density at the center section of the cornea was not observed between the EW-7197 eye drop group and the base agent eye drop group at week 12. Since guttata tended to be higher in the corneal peripheral section than the corneal center section, it is understood that a significant difference in the corneal endothelial density was not observed at the corneal center section between the EW-7197 eye drop group and the base agent eye drop group at week 12. In fact, fibronectin expression levels tended to be higher in the peripheral section than the center section (FIG. 9). As shown in FIG. 9, a clear suppression of fibronectin expression was observed in the 0.02% and 0.1% EW-7197 eye drop groups. When the same experiment was run with a 0.004% (0.1 mM) concentration which is ⅕ of the concentration of 0.02% EW-7197 eye drop in order to test the pharmacological effect at a low concentration, a tendency of suppressing fibronectin expression was observed. This revealed that EW-7197 is effective at a broad range of concentrations.

Example 7: Formulation Example of Cornea Preservation Solution Containing EW-7197

This Example manufactures a cornea preservation solution containing EW-7197 as follows as a Formulation Example.

The preservation solution shown below is prepared by a conventional method.

| EW-7197 | effective amount (e.g., 0.1 μM) |
| Optisol-GS (Bausch-Lomb) | suitable amount |
| Total amount | 100 mL |

Example 8: Preparation Example of Eye Drop

The composition of the tested substance at each concentration is shown below.

| EW-7197 | 0.1 mM |
| Sodium chloride | 0.85 g |
| Sodium dihydrogen phosphate dihydrate | 0.1 g |
| (optionally) Benzalkonium chloride | 0.005 g |
| Sodium hydroxide | suitable amount |
| Purified water | suitable amount |
| Total amount: | 100 mL (pH 7.0) |

The concentration may be diluted using a base agent consisting of the following components.

| Sodium chloride | 0.85 g |
| Sodium dihydrogen phosphate dihydrate | 0.1 g |
| (optionally) Benzalkonium chloride | 0.005 g |
| Sodium hydroxide | suitable amount |
| Purified water | suitable amount |
| Total amount | 100 mL (pH 7.0) |

For example, commercially available components that are in compliance with the Japanese Pharmacopoeia or equivalent thereof can be used as each component other than the active ingredient.

Example 9: Diagnosis and Therapy Example

The present invention is used when diagnosed with Fuchs' endothelial corneal dystrophy or a similar corneal endothelial disease (specific examples thereof include 1) observation of guttae formation, thickening of the Descemet's membrane, corneal epithelial edema, or edema of the corneal stroma by slit-lamp microscopy, 2) observation of images of guttae or corneal endothelial disorder with a specular microscope, 3) observation of corneal edema with a Pentacam, OCT, ultrasonic corneal thickness measuring apparatus, or the like, and 4) when determined as high risk by genetic diagnosis). This can be treated by using the composition of the invention as eye drops, intracameral injection, administration using sustained-release agent, intravitreal injection, or subconjunctival injection.

For example, commercially available components that are in compliance with the Japanese Pharmacopoeia or equivalent thereof can be used as each component other than the active ingredient.

As disclosed above, the present invention is exemplified by the use of its preferred embodiments. However, it is understood that the scope of the present invention should be interpreted solely based on the Claims. It is also understood that any patent, any patent application, and any references cited herein should be incorporated herein by reference in the same manner as the contents are specifically described herein. The present application claims priority to Japanese Patent Application No. 2017-239049 (filed on Dec. 13, 2017) and Japanese Patent Application No. 2018-184783 (filed on Sep. 28, 2018). The entire content thereof is incorporated herein by reference.

INDUSTRIAL APPLICABILITY

A medicament for treating or preventing a corneal endothelial condition, disorder, or disease comprising (T)EW-7197 is provided. In particular, a medicament for treating or preventing a corneal endothelial disorder of Fuchs' endothelial corneal dystrophy is provided. A technology that is available in industries (pharmaceutical industry and the like) involved with technologies related to drug development or the like based on such a technology is provided.

The invention claimed is:

1. A method for treating or preventing a corneal endothelial condition, disorder, or disease, comprising administering to the subject an effective amount of (T)EW-7197 (N-((4-([1,2,4]triazolo[1,5-a]pyridin-6-yl)-5-(6-methylpyridin-2-yl)-1H-imidazol-2-yl)methyl)-2-fluoroaniline), or a pharmaceutically acceptable salt thereof, or a solvate thereof.

2. The method of claim 1, wherein the method suppresses a reduction in a corneal endothelial cell density.

3. The method of claim 1, wherein the corneal endothelial condition, disorder, or disease is Fuchs' endothelial corneal dystrophy or corneal guttata.

4. The method of claim 1, wherein the corneal endothelial condition, disorder, or disease is due to overexpression of extracellular matrix (ECM).

5. The method of claim 4, wherein the extracellular matrix (ECM) is selected from the group consisting of type I collagen, type IV collage, type V collage, and fibronectin.

6. The method of claim 4, wherein the corneal endothelial condition, disorder, or disease is selected from the group consisting of Fuchs' endothelial corneal dystrophy, guttae formation, thickening of a Descemet's membrane, thickening of a cornea, corneal opacity, scar, corneal nebula, corneal macula, leukoma, glare, and blurred vision.

7. The method of claim 1, wherein the corneal endothelial condition, disorder, or disease is in Fuchs' endothelial corneal dystrophy.

8. The method of claim 1, wherein the (T)EW-7197, or a pharmaceutically acceptable salt thereof, or a solvate thereof is administered at a concentration of about 0.001 mM to about 10 mM.

9. The method of claim 1, wherein the (T)EW-7197, or a pharmaceutically acceptable salt thereof, or a solvate thereof is administered at a concentration of about 0.01 mM to about 5 mM.

10. The method of claim 1, wherein the (T)EW-7197, or a pharmaceutically acceptable salt thereof, or a solvate thereof is administered as an eye drop.

* * * * *